US010563977B2

(12) United States Patent
Ohyama et al.

(10) Patent No.: US 10,563,977 B2
(45) Date of Patent: Feb. 18, 2020

(54) THREE-DIMENSIONAL MEASURING DEVICE

(71) Applicant: CKD Corporation, Aichi (JP)

(72) Inventors: Tsuyoshi Ohyama, Aichi (JP); Norihiko Sakaida, Aichi (JP); Ikuo Futamura, Aichi (JP)

(73) Assignee: CKD CORPORATION, Aichi (JP)

( * ) Notice: Subject to any disclaimer, the term of this patent is extended or adjusted under 35 U.S.C. 154(b) by 0 days.

(21) Appl. No.: 16/059,210

(22) Filed: Aug. 9, 2018

(65) Prior Publication Data

US 2019/0025048 A1 Jan. 24, 2019

Related U.S. Application Data

(63) Continuation of application No. PCT/JP2016/075517, filed on Aug. 31, 2016.

(30) Foreign Application Priority Data

Feb. 12, 2016 (JP) .................................. 2016-024318

(51) Int. Cl.
*G01B 11/25* (2006.01)
*H05K 3/34* (2006.01)
(Continued)

(52) U.S. Cl.
CPC .......... *G01B 11/25* (2013.01); *G01B 11/0608* (2013.01); *G01B 11/16* (2013.01);
(Continued)

(58) Field of Classification Search
CPC .. G02B 13/0045; G02B 9/62; G02B 27/0025; G02B 13/18; G02B 27/0172; G02B 9/60;
(Continued)

(56) References Cited

U.S. PATENT DOCUMENTS

| 6,611,344 B1 * | 8/2003 | Chuang .................. G01B 11/24 356/601 |
| 6,614,539 B1 * | 9/2003 | Shimizu .................. G02B 13/22 356/609 |

(Continued)

FOREIGN PATENT DOCUMENTS

| JP | S60-242306 A | 12/1985 |
| JP | 2002-350359 A | 12/2002 |

(Continued)

OTHER PUBLICATIONS

Notification of Reasons for Resusal in counterpart Japanese Patent Application No. 2016-024318, dated Mar. 21, 2017 (6 pages).

(Continued)

*Primary Examiner* — Michael P Stafira
(74) *Attorney, Agent, or Firm* — Osha Liang LLP

(57) ABSTRACT

A three-dimensional measurement device includes: an illuminator that irradiates a measured object with a predetermined light; an imaging device that comprises: an imaging sensor displaceable at least in a vertical direction; and a both-sided telecentric optical system that causes the imaging sensor to form an image of a predetermined area on the measured object irradiated with the predetermined light; a conveyor that moves the illuminator and the imaging device relative to the measured object; and a controller that: executes three-dimensional measurement of a predetermined measurement object on the measured object, based on the taken image; measures a height of the predetermined area at least at a time prior to imaging of the predetermined area under the predetermined light; and changes a height position of the imaging sensor based on a measurement result to adjust an interval between the predetermined area and the imaging sensor to a predetermined distance.

17 Claims, 14 Drawing Sheets

(51) Int. Cl.
 G01B 11/24 (2006.01)
 G01B 11/06 (2006.01)
 G01B 11/16 (2006.01)

(52) U.S. Cl.
 CPC .............. G01B 11/24 (2013.01); H05K 3/34 (2013.01); *G01B 2210/56* (2013.01)

(58) Field of Classification Search
 CPC .. G02B 9/64; G02B 2027/0178; G02B 21/02; G02B 13/02; G02B 13/14; G02B 21/361; G02B 21/367; G02B 9/34; G02B 13/04; G02B 13/06; G02B 2027/0187; G02B 21/26; G02B 26/06; G02B 26/10; G02B 27/0944; G02B 3/04; G02B 5/208; G02B 13/00; G02B 13/0015; G02B 13/004; G02B 13/006; G02B 13/22; G02B 2027/014; G02B 21/0032; G02B 21/006; G02B 27/0037; G02B 27/0075; G02B 27/017; G02B 27/0927; G02B 27/0955; G02B 27/30; G02B 27/425; G02B 5/005; G02B 13/002; G02B 13/0035; G02B 13/0065; G02B 13/008; G02B 13/0095; G02B 13/24; G02B 15/14; G02B 17/0663; G02B 19/0047; G02B 2027/013; G02B 2027/0132; G02B 2027/0134; G02B 2027/0138; G02B 2027/015; G02B 2027/0185; G02B 2027/0194; G02B 21/00; G02B 21/0008; G02B 21/0016; G02B 21/0024; G02B 21/0028; G02B 21/0036; G02B 21/0052; G02B 21/008; G02B 21/06; G02B 21/082; G02B 21/084; G02B 21/12; G02B 21/16; G02B 21/241; G02B 21/244; G02B 21/365; G02B 23/04; G02B 23/2446; G02B 23/2461; G02B 23/26; G02B 26/005; G02B 26/007; G02B 26/008; G02B 26/08; G02B 26/0816; G02B 26/0833; G02B 26/0841; G02B 26/105; G02B 26/121; G02B 27/005; G02B 27/0093; G02B 27/01; G02B 27/0101; G02B 27/0149; G02B 27/0176; G02B 27/0179; G02B 27/0916; G02B 27/0977; G02B 27/0988; G02B 27/106; G02B 27/225; G02B 27/2264; G02B 27/2278; G02B 27/26; G02B 27/4272; G02B 27/44; G02B 27/48; G02B 27/646; G02B 3/0043; G02B 3/0056; G02B 3/0068; G02B 3/02; G02B 3/14; G02B 5/0252; G02B 5/0257; G02B 5/04; G02B 5/08; G02B 5/0891; G02B 5/09; G02B 5/1861; G02B 5/1876; G02B 5/205; G02B 5/32; G02B 6/0073; G02B 6/0076; G02B 7/023; G02B 7/1821; G02B 7/198; G02B 7/28; G02B 9/02091; G02B 11/24; G02B 11/026; G02B 11/14; G02B 11/2441; G02B 11/2513; G02B 11/2518; G02B 2210/58; G02B 5/008; G02B 9/0203; G02B 9/02035; G02B 11/002; G02B 11/005; G02B 11/25; G02B 11/2545; G02B 11/27; G02B 21/042; G02B 21/047; G02B 2290/70; G02B 5/0014; G02B 9/02; G02B 9/2004; G02B 9/02015; G02B 9/02028; G02B 9/02034; G02B 9/02043; G02B 9/02049; G02B 9/02067; G02B 9/02087; G02B 2027/0107; G02B 2027/0116; G02B 2027/0127; G01N 21/6458; G01N 15/06; G01N 1/38; G01N 2015/0693; G01N 2021/6419; G01N 2021/6439; G01N 2021/6465; G01N 2021/6484; G01N 2035/00346; G01N 2035/0443; G01N 2035/0444; G01N 2035/0446; G01N 2035/0455; G01N 2035/1032; G01N 21/255; G01N 21/27; G01N 21/4795; G01N 21/64; G01N 21/6428; G01N 21/6452; G01N 21/6486; G01N 21/95684; G01N 2201/0638; G01N 2201/127; G01N 2458/30; G01N 33/54373; G01N 33/581; G01N 33/582; G01N 35/025; G01N 35/1002; G01J 3/50; G01J 2003/2826; G01J 3/02; G01J 3/0205; G01J 3/0208; G01J 3/0216; G01J 3/0218; G01J 3/0224; G01J 3/0243; G01J 3/0256; G01J 3/10; G01J 3/2823; G01J 3/462; G01J 3/501; G01J 3/508; G01J 3/51; G01J 4/04

See application file for complete search history.

(56) References Cited

U.S. PATENT DOCUMENTS

| | | | |
|---|---|---|---|
| 2010/0008543 A1* | 1/2010 | Yamada | G01B 11/2518 382/106 |
| 2010/0177192 A1* | 7/2010 | Ishigaki | G01B 11/25 348/135 |
| 2016/0103443 A1* | 4/2016 | Bryll | G05B 19/21 700/114 |
| 2016/0153771 A1* | 6/2016 | Aoto | G01B 9/02062 356/497 |
| 2018/0180400 A1* | 6/2018 | Homma | G01B 9/02 |
| 2018/0209784 A1* | 7/2018 | Zhao | G01B 11/24 |
| 2018/0313645 A1* | 11/2018 | Umemura | G01B 11/02 |

FOREIGN PATENT DOCUMENTS

| | | |
|---|---|---|
| JP | 2006-516719 A | 7/2006 |
| JP | 2012-247375 A | 12/2012 |
| JP | 2014-178233 A | 9/2014 |
| JP | 2014-222292 A | 11/2014 |

OTHER PUBLICATIONS

International Search Report for corresponding International Application No. PCT/JP2016/075517, dated Dec. 6, 2016 (5 pages).

* cited by examiner

FIG. 10A

| TIME ↓ | IRRADIATION LIGHT TYPE | | | | | | | | | | |
|---|---|---|---|---|---|---|---|---|---|---|---|
| t1 | PATTERN LIGHT OF 1ST LV | COORDINATE | P17 | P16 | P15 | P14 | P13 | P12 | P11 | P10 | P9 |
| | | PS | 0° | 22.5° | 45° | 67.5° | 90° | 112.5° | 135° | 157.5° | 180° |
| t2 | RED LIGHT OF 1ST LV | COORDINATE | P18 | P17 | P16 | P15 | P14 | P13 | P12 | P11 | P10 |
| | | COLOR | R1 | R1 | R1 | R1 | R1 | R1 | R1 | R1 | R1 |
| t3 | PATTERN LIGHT OF 2ND LV | COORDINATE | P19 | P18 | P17 | P16 | P15 | P14 | P13 | P12 | P11 |
| | | PS | 0° | 22.5° | 45° | 67.5° | 90° | 112.5° | 135° | 157.5° | 180° |
| t4 | RED LIGHT OF 2ND LV | COORDINATE | P20 | P19 | P18 | P17 | P16 | P15 | P14 | P13 | P12 |
| | | COLOR | R2 | R2 | R2 | R2 | R2 | R2 | R2 | R2 | R2 |
| t5 | PATTERN LIGHT OF 1ST LV | COORDINATE | P21 | P20 | P19 | P18 | P17 | P16 | P15 | P14 | P13 |
| | | PS | 0° | 22.5° | 45° | 67.5° | 90° | 112.5° | 135° | 157.5° | 180° |
| t6 | GREEN LIGHT OF 1ST LV | COORDINATE | P22 | P21 | P20 | P19 | P18 | P17 | P16 | P15 | P14 |
| | | COLOR | G1 | G1 | G1 | G1 | G1 | G1 | G1 | G1 | G1 |
| t7 | PATTERN LIGHT OF 2ND LV | COORDINATE | P23 | P22 | P21 | P20 | P19 | P18 | P17 | P16 | P15 |
| | | PS | 0° | 22.5° | 45° | 67.5° | 90° | 112.5° | 135° | 157.5° | 180° |
| t8 | GREEN LIGHT OF 2ND LV | COORDINATE | P24 | P23 | P22 | P21 | P20 | P19 | P18 | P17 | P16 |
| | | COLOR | G2 | G2 | G2 | G2 | G2 | G2 | G2 | G2 | G2 |
| t9 | PATTERN LIGHT OF 1ST LV | COORDINATE | P25 | P24 | P23 | P22 | P21 | P20 | P19 | P18 | P17 |
| | | PS | 0° | 22.5° | 45° | 67.5° | 90° | 112.5° | 135° | 157.5° | 180° |
| t10 | BLUE LIGHT OF 1ST LV | COORDINATE | P26 | P25 | P24 | P23 | P22 | P21 | P20 | P19 | P18 |
| | | COLOR | B1 | B1 | B1 | B1 | B1 | B1 | B1 | B1 | B1 |
| t11 | PATTERN LIGHT OF 2ND LV | COORDINATE | P27 | P26 | P25 | P24 | P23 | P22 | P21 | P20 | P19 |
| | | PS | 0° | 22.5° | 45° | 67.5° | 90° | 112.5° | 135° | 157.5° | 180° |
| t12 | BLUE LIGHT OF 2ND LV | COORDINATE | P28 | P27 | P26 | P25 | P24 | P23 | P22 | P21 | P20 |
| | | COLOR | B2 | B2 | B2 | B2 | B2 | B2 | B2 | B2 | B2 |
| t13 | PATTERN LIGHT OF 1ST LV | COORDINATE | P29 | P28 | P27 | P26 | P25 | P24 | P23 | P22 | P21 |
| | | PS | 0° | 22.5° | 45° | 67.5° | 90° | 112.5° | 135° | 157.5° | 180° |
| t14 | | | | | | | | | | | |
| t15 | PATTERN LIGHT OF 2ND LV | COORDINATE | P31 | P30 | P29 | P28 | P27 | P26 | P25 | P24 | P23 |
| | | PS | 0° | 22.5° | 45° | 67.5° | 90° | 112.5° | 135° | 157.5° | 180° |
| t16 | | | | | | | | | | | |

\* LV: LUMINANCE VALUE    \* PS: PHASE OF STRIPE

FIG. 10B

| TIME ↓ | | IRRADIATION LIGHT TYPE | | | | | | | | |
|---|---|---|---|---|---|---|---|---|---|---|
| t1 | PATTERN LIGHT OF 1ST LV | COORDINATE | P8 | P7 | P6 | P5 | P4 | P3 | P2 | P1 |
| | | PS | 202.5° | 225° | 247.5° | 270° | 292.5° | 315° | 337.5° | 360° |
| t2 | RED LIGHT OF 1ST LV | COORDINATE | P9 | P8 | P7 | P6 | P5 | P4 | P3 | P2 |
| | | COLOR | R1 | R1 | R1 | R1 | R1 | R1 | R1 | R1 |
| t3 | PATTERN LIGHT OF 2ND LV | COORDINATE | P10 | P9 | P8 | P7 | P6 | P5 | P4 | P3 |
| | | PS | 202.5° | 225° | 247.5° | 270° | 292.5° | 315° | 337.5° | 360° |
| t4 | RED LIGHT OF 2ND LV | COORDINATE | P11 | P10 | P9 | P8 | P7 | P6 | P5 | P4 |
| | | COLOR | R2 | R2 | R2 | R2 | R2 | R2 | R2 | R2 |
| t5 | PATTERN LIGHT OF 1ST LV | COORDINATE | P12 | P11 | P10 | P9 | P8 | P7 | P6 | P5 |
| | | PS | 202.5° | 225° | 247.5° | 270° | 292.5° | 315° | 337.5° | 360° |
| t6 | GREEN LIGHT OF 1ST LV | COORDINATE | P13 | P12 | P11 | P10 | P9 | P8 | P7 | P6 |
| | | COLOR | G1 | G1 | G1 | G1 | G1 | G1 | G1 | G1 |
| t7 | PATTERN LIGHT OF 2ND LV | COORDINATE | P14 | P13 | P12 | P11 | P10 | P9 | P8 | P7 |
| | | PS | 202.5° | 225° | 247.5° | 270° | 292.5° | 315° | 337.5° | 360° |
| t8 | GREEN LIGHT OF 2ND LV | COORDINATE | P15 | P14 | P13 | P12 | P11 | P10 | P9 | P8 |
| | | COLOR | G2 | G2 | G2 | G2 | G2 | G2 | G2 | G2 |
| t9 | PATTERN LIGHT OF 1ST LV | COORDINATE | P16 | P15 | P14 | P13 | P12 | P11 | P10 | P9 |
| | | PS | 202.5° | 225° | 247.5° | 270° | 292.5° | 315° | 337.5° | 360° |
| t10 | BLUE LIGHT OF 1ST LV | COORDINATE | P17 | P16 | P15 | P14 | P13 | P12 | P11 | P10 |
| | | COLOR | B1 | B1 | B1 | B1 | B1 | B1 | B1 | B1 |
| t11 | PATTERN LIGHT OF 2ND LV | COORDINATE | P18 | P17 | P16 | P15 | P14 | P13 | P12 | P11 |
| | | PS | 202.5° | 225° | 247.5° | 270° | 292.5° | 315° | 337.5° | 360° |
| t12 | BLUE LIGHT OF 2ND LV | COORDINATE | P19 | P18 | P17 | P16 | P15 | P14 | P13 | P12 |
| | | COLOR | B2 | B2 | B2 | B2 | B2 | B2 | B2 | B2 |
| t13 | PATTERN LIGHT OF 1ST LV | COORDINATE | P20 | P19 | P18 | P17 | P16 | P15 | P14 | P13 |
| | | PS | 202.5° | 225° | 247.5° | 270° | 292.5° | 315° | 337.5° | 360° |
| t14 | | | | | | | | | | |
| t15 | PATTERN LIGHT OF 2ND LV | COORDINATE | P22 | P21 | P20 | P19 | P18 | P17 | P16 | P15 |
| | | PS | 202.5° | 225° | 247.5° | 270° | 292.5° | 315° | 337.5° | 360° |
| t16 | | | | | | | | | | |

\* LV: LUMINANCE VALUE   \* PS: PHASE OF STRIPE

FIG. 11A

| | | | | | | | | | | | | | | | | | | |
|---|---|---|---|---|---|---|---|---|---|---|---|---|---|---|---|---|---|---|
| PATTERN LIGHT OF 1ST LV | COORDINATE | . | . | . | . | . | . | . | . | . | . | . | . | . | . | . | . | P17 |
| | PS | | | | | | | | | | | | | | | | | 0° |
| RED LIGHT OF 1ST LV | COORDINATE | . | . | . | . | . | . | . | . | . | . | . | . | . | . | . | P18 | P17 |
| | COLOR | | | | | | | | | | | | | | | | R1 | R1 |
| PATTERN LIGHT OF 2ND LV | COORDINATE | . | . | . | . | . | . | . | . | . | . | . | . | . | . | P19 | P18 | P17 |
| | PS | | | | | | | | | | | | | | | 0° | 22.5° | 45° |
| RED LIGHT OF 2ND LV | COORDINATE | . | . | . | . | . | . | . | . | . | . | . | . | . | P20 | P19 | P18 | P17 |
| | COLOR | | | | | | | | | | | | | | R2 | R2 | R2 | R2 |
| PATTERN LIGHT OF 1ST LV | COORDINATE | . | . | . | . | . | . | . | . | . | . | . | . | P21 | P20 | P19 | P18 | P17 |
| | PS | | | | | | | | | | | | | 0° | 22.5° | 45° | 67.5° | 90° |
| GREEN LIGHT OF 1ST LV | COORDINATE | . | . | . | . | . | . | . | . | . | . | . | P22 | P21 | P20 | P19 | P18 | P17 |
| | COLOR | | | | | | | | | | | | G1 | G1 | G1 | G1 | G1 | G1 |
| PATTERN LIGHT OF 2ND LV | COORDINATE | . | . | . | . | . | . | . | . | . | . | P23 | P22 | P21 | P20 | P19 | P18 | P17 |
| | PS | | | | | | | | | | | 0° | 22.5° | 45° | 67.5° | 90° | 112.5° | 135° |
| GREEN LIGHT OF 2ND LV | COORDINATE | . | . | . | . | . | . | . | . | . | P24 | P23 | P22 | P21 | P20 | P19 | P18 | P17 |
| | COLOR | | | | | | | | | | G2 | G2 | G2 | G2 | G2 | G2 | G2 | G2 |
| PATTERN LIGHT OF 1ST LV | COORDINATE | . | . | . | . | . | . | . | . | P25 | P24 | P23 | P22 | P21 | P20 | P19 | P18 | P17 |
| | PS | | | | | | | | | 0° | 22.5° | 45° | 67.5° | 90° | 112.5° | 135° | 157.5° | 180° |
| BLUE LIGHT OF 1ST LV | COORDINATE | . | . | . | . | . | . | . | P26 | P25 | P24 | P23 | P22 | P21 | P20 | P19 | P18 | P17 |
| | COLOR | | | | | | | | B1 | B1 | B1 | B1 | B1 | B1 | B1 | B1 | B1 | B1 |
| PATTERN LIGHT OF 2ND LV | COORDINATE | . | . | . | . | . | . | P27 | P26 | P25 | P24 | P23 | P22 | P21 | P20 | P19 | P18 | P17 |
| | PS | | | | | | | 0° | 22.5° | 45° | 67.5° | 90° | 112.5° | 135° | 157.5° | 180° | 202.5° | 225° |
| BLUE LIGHT OF 2ND LV | COORDINATE | . | . | . | . | . | P28 | P27 | P26 | P25 | P24 | P23 | P22 | P21 | P20 | P19 | P18 | P17 |
| | COLOR | | | | | | B2 | B2 | B2 | B2 | B2 | B2 | B2 | B2 | B2 | B2 | B2 | B2 |
| PATTERN LIGHT OF 1ST LV | COORDINATE | . . . . . | | | | P29 | P28 | P27 | P26 | P25 | P24 | P23 | P22 | P21 | P20 | P19 | P18 | P17 |
| | PS | | | | | 0° | 22.5° | 45° | 67.5° | 90° | 112.5° | 135° | 157.5° | 180° | 202.5° | 225° | 247.5° | 270° |
| PATTERN LIGHT OF 2ND LV | COORDINATE | P31 | P30 | P29 | P28 | P27 | P26 | P25 | P24 | P23 | P22 | P21 | P20 | P19 | P18 | P17 |
| | PS | 0° | 22.5° | 45° | 67.5° | 90° | 112.5° | 135° | 157.5° | 180° | 202.5° | 225° | 247.5° | 270° | 292.5° | 315° |

*LV: LUMINANCE VALUE    *PS: PHASE OF STRIPE

FIG. 11B

| Row | | P16 | P15 | P14 | P13 | P12 | P11 | P10 | P9 | P8 | P7 | P6 | P5 | P4 | P3 | P2 | P1 |
|---|---|---|---|---|---|---|---|---|---|---|---|---|---|---|---|---|---|
| PATTERN LIGHT OF 1ST LV | COORDINATE | P16 | P15 | P14 | P13 | P12 | P11 | P10 | P9 | P8 | P7 | P6 | P5 | P4 | P3 | P2 | P1 |
| | PS | 22.5° | 45° | 67.5° | 90° | 112.5° | 135° | 157.5° | 180° | 202.5° | 225° | 247.5° | 270° | 292.5° | 315° | 337.5° | 360° |
| RED LIGHT OF 1ST LV | COORDINATE | P16 | P15 | P14 | P13 | P12 | P11 | P10 | P9 | P8 | P7 | P6 | P5 | P4 | P3 | P2 | ... |
| | COLOR | R1 | R1 | R1 | R1 | R1 | R1 | R1 | R1 | R1 | R1 | R1 | R1 | R1 | R1 | R1 | |
| PATTERN LIGHT OF 2ND LV | COORDINATE | P16 | P15 | P14 | P13 | P12 | P11 | P10 | P9 | P8 | P7 | P6 | P5 | P4 | P3 | | |
| | PS | 67.5° | 90° | 112.5° | 135° | 157.5° | 180° | 202.5° | 225° | 247.5° | 270° | 292.5° | 315° | 337.5° | 360° | | |
| RED LIGHT OF 2ND LV | COORDINATE | P16 | P15 | P14 | P13 | P12 | P11 | P10 | P9 | P8 | P7 | P6 | P5 | P4 | | | |
| | COLOR | R2 | R2 | R2 | R2 | R2 | R2 | R2 | R2 | R2 | R2 | R2 | R2 | R2 | | | |
| PATTERN LIGHT OF 1ST LV | COORDINATE | P16 | P15 | P14 | P13 | P12 | P11 | P10 | P9 | P8 | P7 | P6 | P5 | | | | |
| | PS | 112.5° | 135° | 157.5° | 180° | 202.5° | 225° | 247.5° | 270° | 292.5° | 315° | 337.5° | 360° | | | | |
| GREEN LIGHT OF 1ST LV | COORDINATE | P16 | P15 | P14 | P13 | P12 | P11 | P10 | P9 | P8 | P7 | P6 | | | | | |
| | COLOR | G1 | G1 | G1 | G1 | G1 | G1 | G1 | G1 | G1 | G1 | G1 | | | | | |
| PATTERN LIGHT OF 2ND LV | COORDINATE | P16 | P15 | P14 | P13 | P12 | P11 | P10 | P9 | P8 | P7 | | | | | | |
| | PS | 157.5° | 180° | 202.5° | 225° | 247.5° | 270° | 292.5° | 315° | 337.5° | 360° | | | | | | |
| GREEN LIGHT OF 2ND LV | COORDINATE | P16 | P15 | P14 | P13 | P12 | P11 | P10 | P9 | P8 | | | | | | | |
| | COLOR | G2 | G2 | G2 | G2 | G2 | G2 | G2 | G2 | G2 | | | | | | | |
| PATTERN LIGHT OF 1ST LV | COORDINATE | P16 | P15 | P14 | P13 | P12 | P11 | P10 | P9 | | | | | | | | |
| | PS | 202.5° | 225° | 247.5° | 270° | 292.5° | 315° | 337.5° | 360° | | | | | | | | |
| BLUE LIGHT OF 1ST LV | COORDINATE | P16 | P15 | P14 | P13 | P12 | P11 | P10 | | | | | | | | | |
| | COLOR | B1 | B1 | B1 | B1 | B1 | B1 | B1 | | | | | | | | | |
| PATTERN LIGHT OF 2ND LV | COORDINATE | P16 | P15 | P14 | P13 | P12 | P11 | | | | | | | | | | |
| | PS | 247.5° | 270° | 292.5° | 315° | 337.5° | 360° | | | | | | | | | | |
| BLUE LIGHT OF 2ND LV | COORDINATE | P16 | P15 | P14 | P13 | P12 | | | | | | | | | | | |
| | COLOR | B2 | B2 | B2 | B2 | B2 | | | | | | | | | | | |
| PATTERN LIGHT OF 1ST LV | COORDINATE | P16 | P15 | P14 | P13 | | | | | | | | | | | | |
| | PS | 292.5° | 315° | 337.5° | 360° | | | | | | | | | | | | |
| PATTERN LIGHT OF 2ND LV | COORDINATE | P16 | P15 | | | | | | | | | | | | | | |
| | PS | 337.5° | 360° | | | | | | | | | | | | | | |

\* LV: LUMINANCE VALUE   \* PS: PHASE OF STRIPE

FIG. 12A

|  |  | P31 | P30 | P29 | P28 | P27 | P26 | P25 | P24 | P23 | P22 |
|---|---|---|---|---|---|---|---|---|---|---|---|
| 1ST GROUP DATA | 1ST TIME ($\theta$+0°) |  |  |  |  |  |  |  |  |  |  |
|  | 2ND TIME ($\theta$+90°) |  |  |  |  |  |  |  |  |  |  |
|  | 3RD TIME ($\theta$+180°) |  |  |  |  |  |  |  |  |  |  |
|  | 4TH TIME ($\theta$+270°) |  |  |  |  |  |  |  |  |  |  |
| 2ND GROUP DATA | 1ST TIME ($\theta$+0°) |  |  |  |  |  |  |  |  |  |  |
|  | 2ND TIME ($\theta$+90°) |  |  |  |  |  |  |  |  |  |  |
|  | 3RD TIME ($\theta$+180°) |  |  |  |  |  |  |  |  |  |  |
|  | 4TH TIME ($\theta$+270°) |  |  |  |  |  |  |  |  |  |  |
| 3RD GROUP DATA | RED |  |  |  |  |  |  |  |  |  |  |
|  | GREEN |  |  |  |  |  |  |  |  |  |  |
|  | BLUE |  |  |  |  |  |  |  |  |  |  |
| 4TH GROUP DATA | RED |  |  |  |  |  |  |  |  |  |  |
|  | GREEN |  |  |  |  |  |  |  |  |  |  |
|  | BLUE |  |  |  |  |  |  |  |  |  |  |

FIG. 12B

|  |  | P21 | P20 | P19 | P18 | P17 | P16 | P15 | P14 | P13 | P12 |
|---|---|---|---|---|---|---|---|---|---|---|---|
| 1ST GROUP DATA | 1ST TIME ($\theta$ +0°) |  |  |  | ... | 0° | ... |  |  |  |  |
|  | 2ND TIME ($\theta$ +90°) |  |  |  | ... | 90° | ... |  |  |  |  |
|  | 3RD TIME ($\theta$ +180°) |  |  |  | ... | 180° | ... |  |  |  |  |
|  | 4TH TIME ($\theta$ +270°) |  |  |  | ... | 270° | ... |  |  |  |  |
| 2ND GROUP DATA | 1ST TIME ($\theta$ +0°) |  |  |  | ... | 45° | ... |  |  |  |  |
|  | 2ND TIME ($\theta$ +90°) |  |  |  | ... | 135° | ... |  |  |  |  |
|  | 3RD TIME ($\theta$ +180°) |  |  |  | ... | 225° | ... |  |  |  |  |
|  | 4TH TIME ($\theta$ +270°) |  |  |  | ... | 315° | ... |  |  |  |  |
| 3RD GROUP DATA | RED |  |  |  | ... | R1 | ... |  |  |  |  |
|  | GREEN |  |  |  | ... | G1 | ... |  |  |  |  |
|  | BLUE |  |  |  | ... | B1 | ... |  |  |  |  |
| 4TH GROUP DATA | RED |  |  |  | ... | R2 | ... |  |  |  |  |
|  | GREEN |  |  |  | ... | G2 | ... |  |  |  |  |
|  | BLUE |  |  |  | ... | B2 | ... |  |  |  |  |

THREE-DIMENSIONAL MEASURING DEVICE

BACKGROUND

Technical Field

The present disclosure relates to a three-dimensional measurement device configured to execute three-dimensional measurement.

Description of Related Art

In general, when electronic components are to be mounted on a printed circuit board, solder paste is printed on a predetermined electrode pattern provided on the printed circuit board. The electronic components are then temporarily fastened on the printed circuit board by taking advantage of the viscosity of the solder paste. The printed circuit board is subsequently introduced into a reflow furnace and is subjected to a predetermined reflow process to achieve soldering. Recently there has been a need to inspect the printing condition of solder paste in a stage prior to introduction into the reflow furnace. A three-dimensional measurement device may be used for this inspection.

Various contactless three-dimensional measurement devices using light have been proposed lately. For example, three-dimensional measurement devices employing the phase shift method are known well.

A known three-dimensional measurement device using the phase shift method includes, for example, a moving mechanism configured to move a measured object, an irradiation device configured to irradiate the measured object with striped pattern light, and an imaging device configured to take an image of the measured object irradiated with the pattern light (as described in, for example, Patent Literature 1). The imaging device is comprised of, for example, a lens and an imaging element.

This three-dimensional measurement device obtains a plurality of image data having different light intensity distributions on the measured object that are different from each other by every predetermined phase of the pattern light, by relatively moving the measured object to a measurement head comprised of the irradiation device and the imaging device. Three-dimensional measurement of the measured object is then executed by the phase shift method, based on the plurality of image data.

For example, when four different image data obtained have light intensity distributions on a measured object that are different from one another by the phase of 90 degrees each of the pattern light, luminance values $I_0$, $I_1$, $I_2$ and $I_3$ of the four different image data at a predetermined coordinate position on the measured object are expressed by Expressions (1), (2), (3) and (4) given below:

$$I_0 = \alpha \sin \theta + \beta \quad (1)$$

$$I_1 = \alpha \sin(\theta + 90°) + \beta = \alpha \cos \theta + \beta \quad (2)$$

$$I_2 = \alpha \sin(\theta + 180°) + \beta = -\alpha \sin \theta + \beta \quad (3)$$

$$I_3 = \alpha \sin(\theta + 270°) + \beta = -\alpha \cos \theta + \beta \quad (4)$$

where $\alpha$ represents a gain, $\beta$ represents an offset, and $\theta$ represents a phase of pattern light.

Expression (5) given below is derived by solving Expressions (1), (2), (3) and (4) for the phase $\theta$:

$$\theta = \tan^{-1}\{(I_0 - I_2)/(I_1 - I_3)\} \quad (5)$$

A height (Z) at each coordinates (X,Y) on the measured object can be determined by using the phase $\theta$ calculated as described above, based on the principle of triangulation.

When a measured object such as a printed circuit board has a warpage or the like, however, there is a difficulty in placing the entire measured object within a focusing range. This may cause partly out-of-focus image data to be obtained and is thus likely to decrease the measurement accuracy.

A recently proposed technique relatively moves and adjusts a measurement head comprised of an irradiation device and an imaging device in a height direction (Z-axis direction), such as to maintain a constant interval between a measured object and the imaging device (as described in, for example, Patent Literature 2).

CITATION LIST

Patent Literature

PTL 1: JP 2012-247375A
PTL 2: JP 2006-516719A

In the configuration that relatively moves the entire measurement head in the height direction like cited Literature 2, a heavy substance is to be moved up and down whether the measurement head itself is moved or a table with the measured object placed thereon is moved. This causes difficulty in making minute movements and quick movements and is thus likely to decrease the measurement accuracy and the measurement speed. Additionally, a large-scale mechanism is required to move the entire measurement head or the entire table and is thus likely to cause size expansion of the apparatus.

This is not characteristic of three-dimensional measurement of the solder paste or the like printed on the printed circuit board but may arise in the field of other three-dimensional measurement devices. This is naturally not characteristic of the phase shift method.

SUMMARY

A three-dimensional measurement device according to one or more embodiments of the present invention improves the measurement accuracy and the like in three-dimensional measurement.

Embodiments of the present invention are described. Functions and advantageous effects according to one or more embodiments of the present invention are also described as appropriate.

A three-dimensional measurement device according to one or more embodiments of the present invention comprises: an irradiation unit configured to irradiate a measured object (for example, a printed circuit board) with a predetermined light (for example, striped pattern light); an imaging unit including an imaging element provided to be displaceable at least in a vertical direction (direction of an optical axis) and a both-sided telecentric optical system configured to cause the imaging element to form an image of a predetermined area on the measured object irradiated with the predetermined element; a moving unit configured to move the irradiation unit and the imaging unit relative to the measured object; an imaging processing unit configured to execute three-dimensional measurement of a predetermined measurement object (for example, solder paste) on the measured object, based on an image taken by the imaging unit; a measurement unit configured to measure a height of the predetermined area (for example, height of a base substrate) in at least a stage prior to imaging of the predetermined area on the measured object under the predetermined light; and an adjustment unit configured to adjust a height position of the imaging element, based on a measurement result of the measurement unit, such that (i.e., until) an interval between the predetermined area and the imaging element becomes equal to a predetermined distance (distance such as to place the predetermined area in a focusing range) in imaging of the predetermined area.

The configuration according to one or more embodiments of the present invention takes an image of a predetermined area (imaging area) on the measured object with adjusting the height position of the imaging element to the predetermined area. This enables a focused image to be obtained constantly. As a result, even when the measured object has a warpage or the like, this configuration enables the entire measured object to be within the focusing range (i.e., enables a focused image to be obtained with regard to the entire measured object) and thereby improves the measurement accuracy.

Especially, the configuration according to one or more embodiments of the present invention moves up and down only the imaging element to maintain the fixed distance between the measured object and the imaging element. This allows for significant downsizing of the mechanism involved in height adjustment (Z-axis direction), compared with the prior art configuration. This also allows for minute and quick movements and thus significantly improves the measurement accuracy and the measurement speed.

Additionally, this configuration executes height adjustment by using the both-sided telecentric optical system and accordingly reduces the effect on the magnification caused by, for example, a position change of the imaging element in the height direction and a height change of the surface of the measured object.

In the three-dimensional measurement device according to one or more embodiments of the present invention, the measurement unit may be configured to measure an inclination of the predetermined area in at least the stage prior to imaging of the predetermined area on the measured object under the predetermined light. The adjustment unit may be configured to adjust an inclination (attitude) of the imaging element, based on a measurement result of the measurement unit, such that (i.e., until) the inclination of the imaging element corresponds to the inclination of the predetermined area in imaging of the predetermined area.

When the measured object has a warpage or the like and the predetermined area (imaging area) on the measured object is inclined, there may be a difficulty in placing the entire field of view of the imaging unit to be within the focusing range. For this reason, it is conventionally required to incline the entire imaging unit (imaging device) according to the warpage or the like of the measured object and focus an image in the entire field of view.

When the entire imaging unit is inclined, however, the field of view of the imaging unit is likely to be deviated (out of the predetermined area). This conventional configuration controls the attitude of the heavy entire imaging unit. This causes difficulty in making minute movements and quick movements and is likely to decrease the measurement accuracy and the measurement speed. This also requires a large-size mechanism to move the entire imaging unit and is thus likely to cause size expansion of the apparatus.

The configuration according to one or more embodiments of the present invention, on the other hand, takes an image of the predetermined area (imaging area) on the measured object with adjusting the inclination of the imaging element to the predetermined area. Even when the predetermined area on the measured object is inclined, this configuration enables an image focused in the entire field of view of the imaging unit to be obtained. As a result, even when the measured object has a warpage or the like, this configuration enables the entire measured object to be within the focusing range (i.e., enables a focused image to be obtained with regard to the entire measured object) and thereby improves the measurement accuracy.

Especially, the configuration according to one or more embodiments of the present invention executes inclination adjustment of only the imaging element. This allows for significant downsizing of the mechanism involved in inclination adjustment, compared with the prior art configuration. This also allows for minute and quick movements and thus significantly improves the measurement accuracy and the measurement speed.

Additionally, this configuration executes inclination adjustment by using the both-sided telecentric optical system and accordingly reduces the effect on the magnification caused by, for example, inclination of the imaging element.

The three-dimensional measurement device according to one or more embodiments of the present invention may further comprise a correction unit configured to correct the image taken by the imaging unit, based on an amount of positional deviation in a horizontal direction of each pixel when the imaging element is inclined.

When the imaging element is inclined from a reference attitude (horizontal attitude), the position of each pixel in the horizontal direction is deviated. This causes a deviation in the positional relationship between each pixel of the imaging element and the corresponding coordinate position on the measured object. Three-dimensional measurement based on the image taken in this state of deviation is likely to decrease the measurement accuracy.

The configuration according to one or more embodiments of the present invention, on the other hand, corrects the deviation of the image data caused by the positional deviation of each pixel in the horizontal direction in the case of inclination of the imaging element by the software-based arithmetic operation and thus suppresses reduction of the measurement accuracy.

The configuration according to one or more embodiments of the present invention uses the both-sided telecentric optical system and causes the imaging element to receive the light that is parallel to the optical axis. Accordingly, by obtaining the amount of inclination of the imaging element, the amount of horizontal deviation of each pixel can be determined accurately according to a simple computation expression. This configuration thus readily provides the correspondence relationship of each pixel of the imaging element to the coordinate position on the measured object. As a result, this reduces the load of the control process.

In the three-dimensional measurement device according to one or more embodiments of the present invention, the moving unit may be configured to reciprocate the irradiation unit and the imaging unit relative to the measured object along a predetermined direction. Measurement of the predetermined area on the measured object by the measurement unit may be executed in a forward path, and adjustment of the predetermined area by the adjustment unit and imaging under the predetermined light may be executed in a backward path.

The configuration according to one or more embodiments of the present invention can execute measurement by the measurement unit in the flow of one identical direction (in the forward path) and execute imaging under the predetermined light in the flow of another identical direction (in the backward path) with regard to all the areas on the measured object. This configuration reduces the measurement error and the like caused by the different moving directions and improves the measurement accuracy (position accuracy).

In the three-dimensional measurement device according to one or more embodiments of the present invention, the measured object may be a printed circuit board with solder paste printed thereon or a wafer substrate with a solder bump formed thereon.

The configuration according to one or more embodiments of the present invention can execute, for example, three-dimensional measurement of the solder paste printed on the printed circuit board or the solder bump formed on the wafer substrate. This configuration can thus determine the good/poor quality of the solder paste or the solder bump, based on the measurement value, in inspection of the solder paste or the solder bump. This configuration provides the functions and the advantageous effects described above in this inspection and ensures determination of the good/poor quality with high accuracy. As a result, this improves the inspection accuracy in a solder printing inspection apparatus or in a solder bump inspection apparatus.

BRIEF DESCRIPTION OF DRAWINGS

FIGS. 10A, 10B are correspondence tables illustrating types of irradiation lights that change with elapse of time and specifications of the irradiation lights at respective coordinate positions on the printed circuit board according to one or more embodiments of the present invention;

FIGS. 11A, 11B are tables schematically illustrating the state of position adjustment of coordinate positions with regard to a plurality of image data according to one or more embodiments of the present invention; and FIGS. 12A, 12B are tables schematically illustrating various data with regard to the respective coordinate positions on the printed circuit board, which are organized in respective categories and rearranged, according to one or more embodiments of the present invention.

DETAILED DESCRIPTION OF EMBODIMENTS

The following describes embodiments of the present invention with reference to the drawings. The configuration of a printed circuit board as a measured object is described first in detail.

Figure 2:
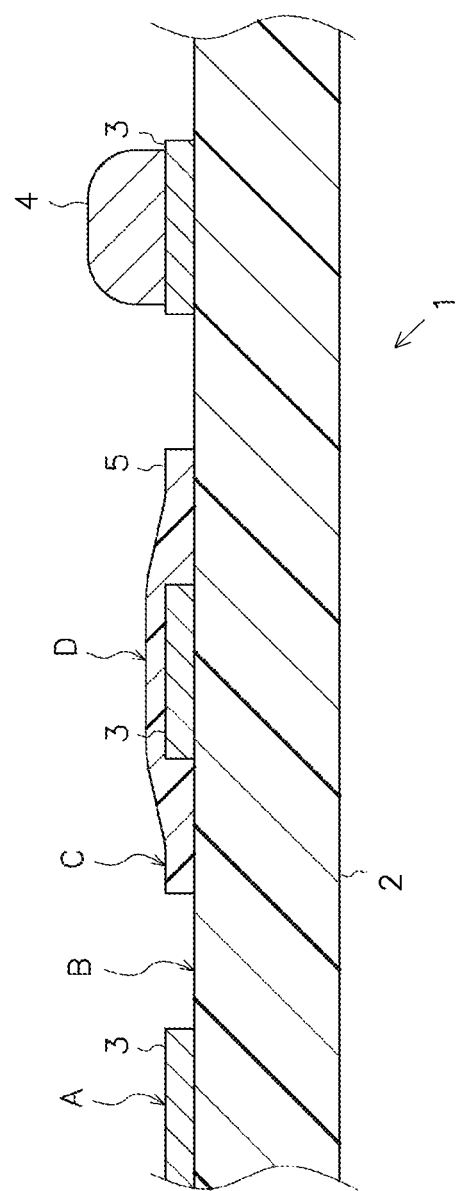
FIG. 2 is a sectional view illustrating a printed circuit board according to one or more embodiments of the present invention.

As shown in FIG. 2, a printed circuit board 1 includes an electrode pattern 3 made of copper foil and provided on a flat plate-like base substrate 2 that is made of, for example, a glass/epoxy resin. Solder paste 4 is further printed on the predetermined electrode pattern 3. An area where this solder paste 4 is printed is called "solder printed area". A remaining part other than the solder printed area is collectively called "background area". This background area includes an area where the electrode pattern 3 is exposed (shown by a symbol A), an area where the base substrate 2 is exposed (shown by a symbol B), an area where a resist film 5 is placed to coat on the base substrate 2 (shown by a symbol C), and an area where a resist film 5 is placed to coat the electrode pattern 3 (shown by a symbol D). The surface of the printed circuit board 1 is coated with the resist film 5, in order to prevent the solder paste 4 from being mounted on any part other than a predetermined wiring part.

Figure 1:
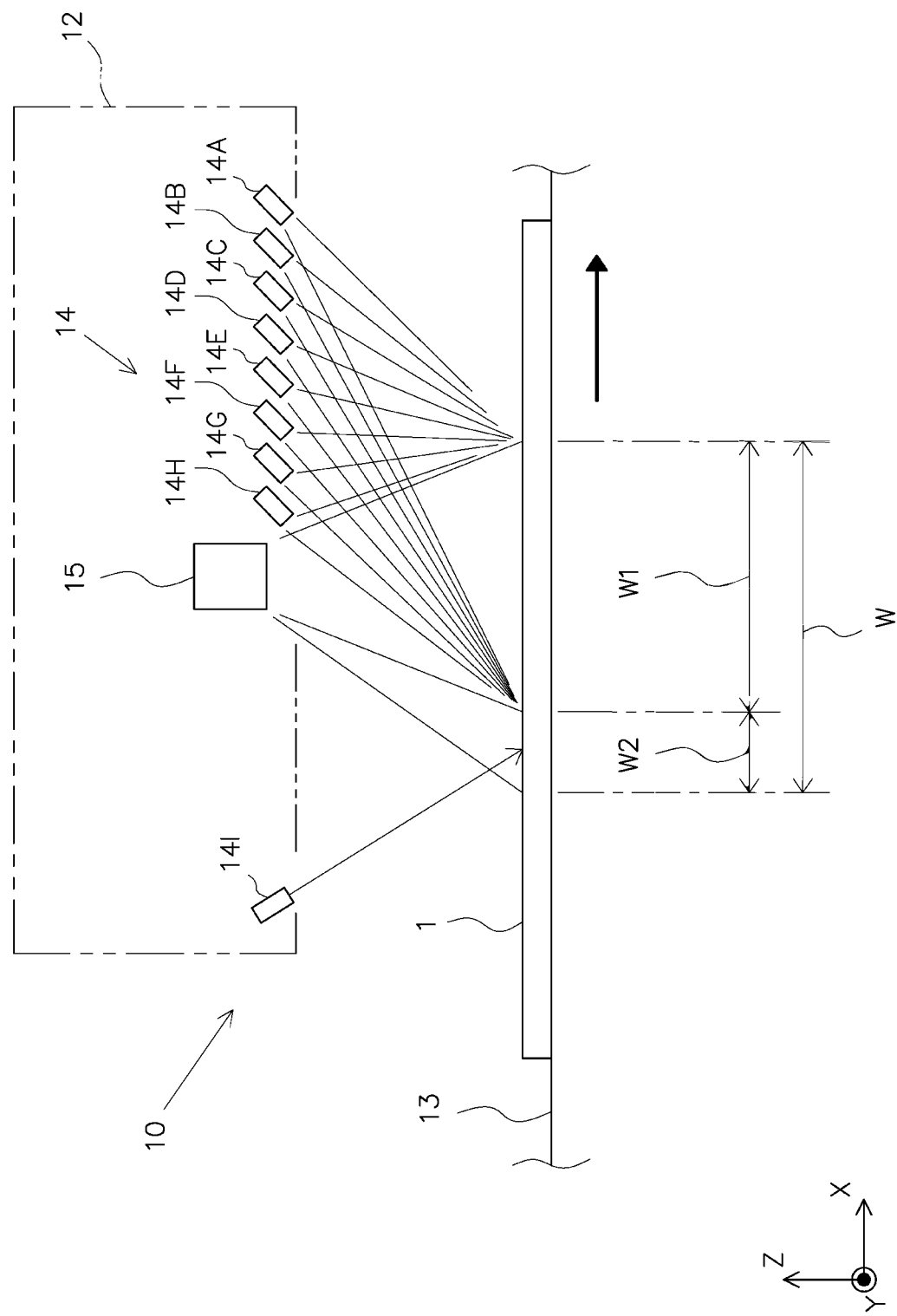
FIG. 1 is a schematic configuration diagram schematically illustrating a substrate inspection apparatus according to one or more embodiments of the present invention.

The following describes a substrate inspection apparatus equipped with a three-dimensional measurement device according to one or more embodiments in detail. FIG. 1 is a schematic configuration diagram schematically illustrating a substrate inspection apparatus 10.

Figure 5:
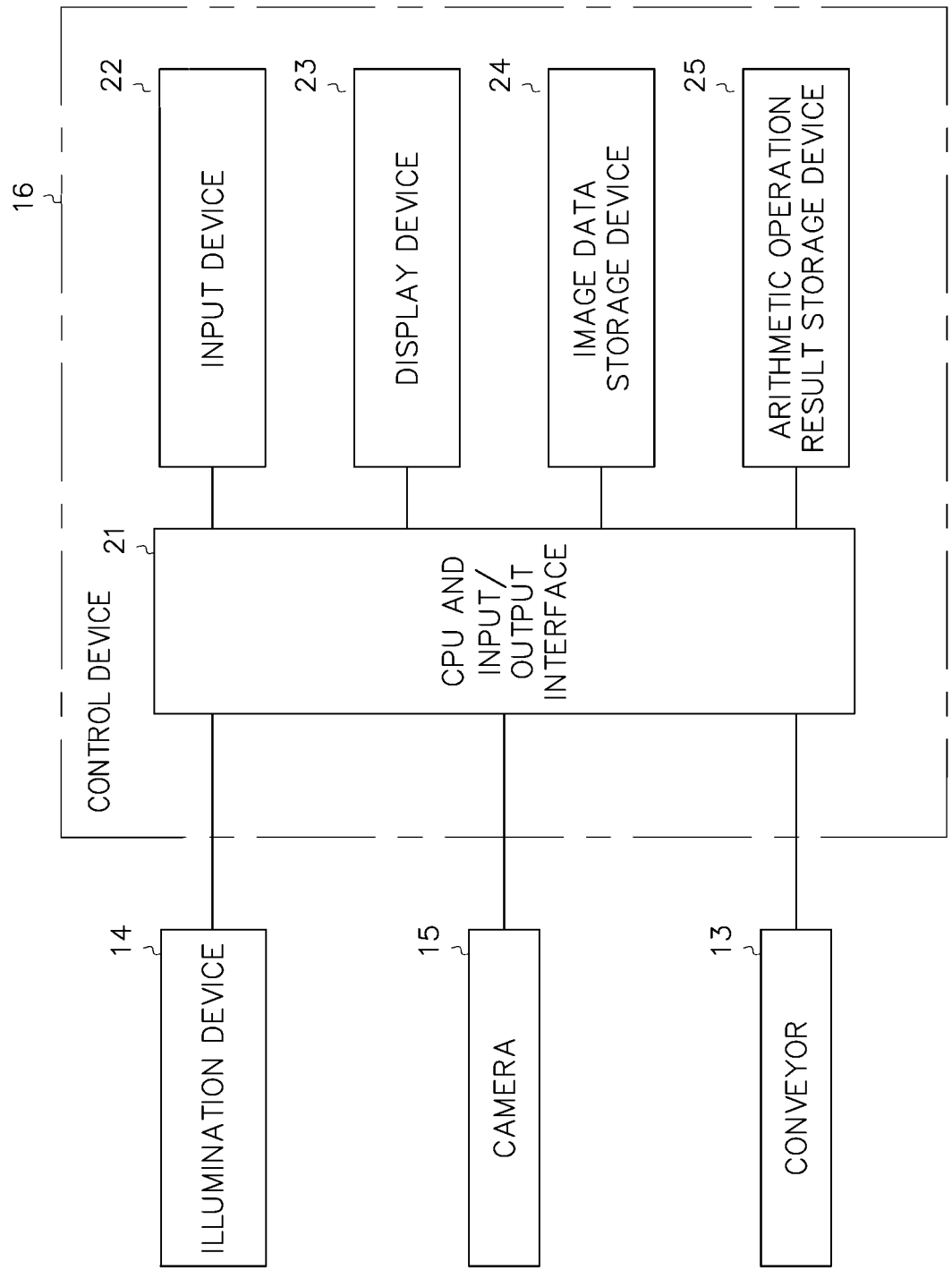
FIG. 5 is a block diagram illustrating the schematic configuration of the substrate inspection apparatus according to one or more embodiments of the present invention.

The substrate inspection apparatus 10 includes a conveyor 13 serving as a moving unit configured to move the printed circuit board 1, an illumination device (illuminator) 14 serving as an irradiation unit configured to irradiate the surface of the printed circuit board 1 obliquely downward with various lights, a camera 15 serving as an imaging unit or an imaging device configured to take an image of the printed circuit board 1 irradiate with the various lights, and a control device 16 configured to execute various controls, image processing and arithmetic operations in the substrate inspection apparatus 10, for example, drive control of the conveyor 13, the illumination device 14 and the camera 15 (as shown in FIG. 5).

The conveyor 13 is equipped with a driving unit such as a motor (not shown). The motor is driven and controlled by the control device 16, so as to horizontally move the printed circuit board 1 placed on the conveyor 13, along an X-axis direction (left-right direction in FIG. 1).

In measurement, the printed circuit board 1 is continuously moved at a fixed speed rightward in the X-axis direction. This causes an imaging range (field of view) W of the camera 15 in the X-axis direction to be moved relative to the printed circuit board 1 in an opposite direction (leftward in the X-axis direction).

The illumination device 14 and the camera 15 are integrated with each other to form a measurement head 12. The measurement head 12 is provided to be horizontally movable in a Y-axis direction (depth direction in FIG. 1) that is orthogonal to the X-axis direction by a non-illustrated driving unit.

Figure 3:
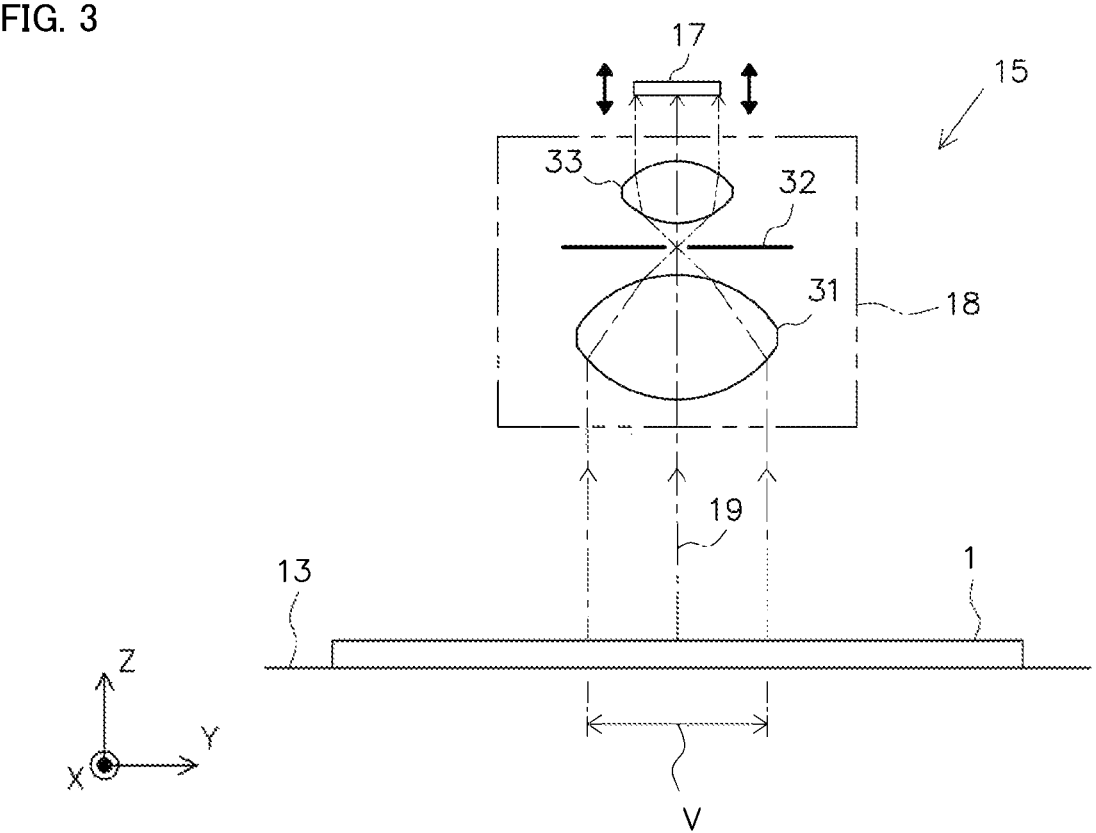
FIG. 3 is a schematic configuration diagram illustrating a camera according to one or more embodiments of the present invention.

On termination of measurement in an entire range in the X-axis direction of the printed circuit board 1 with regard to a predetermined range V in the Y-axis direction of the printed circuit board 1 (imaging range (field of view) V of the camera 15 in the Y-axis direction as shown in FIG. 3) with continuously moving the printed circuit board 1 rightward in the X-axis direction, the printed circuit board 1 is moved in the opposite direction (leftward in the X-axis direction) to be returned to its initial position. Simultaneously, the measurement head 12 is moved by a predetermined amount along the Y-axis direction. Subsequently measurement is executed in the entire range in the X-axis direction of the printed circuit board 1, while the printed circuit board 1 is continuously moved rightward in the X-axis direction, like the foregoing procedure. Measurement in the entire range in the X-axis direction of the printed circuit board 1 with sequentially shifting the measurement head 12 in the Y-axis direction in this manner achieves measurement of the entire area of the printed circuit board 1.

The illumination device 14 includes nine lighting units (a first lighting unit 14A to a ninth lighting unit 14I). The first lighting unit 14A to the ninth lighting unit 14I are respectively known lighting units and are thus not described in detail with reference drawings.

Among them, the first lighting unit 14A and the second lighting unit 14B are configured to radiate predetermined pattern light. The first lighting unit 14A and the second lighting unit 14B include, for example, a light source configured to emit predetermined light and a liquid crystal optical shutter configured to convert the light from the light source into pattern light.

The light emitted from the light source is guided to a condenser lens to be converted to parallel light and is subsequently guided to a projection lens via the liquid crystal optical shutter to be radiated as striped pattern light. Using the liquid crystal optical shutter enables generation of pattern light having a light intensity distribution near to a sinusoidal wave and enhances the measurement resolving power of three-dimensional measurement.

According to one or more embodiments, the radiated pattern light has stripes in a direction parallel to the Y-axis direction that is orthogonal to the moving direction of the printed circuit board 1 (X-axis direction). This causes the printed circuit board 1 to be irradiated with the pattern light having the striped (sinusoidal) light intensity distribution along its moving direction. According to one or more embodiments, this pattern light is used as measurement light for three-dimensional measurement of, for example, the solder paste 4.

The pattern light radiated from the first lighting unit 14A and the pattern light radiated from the second lighting unit 14B, however, have different luminance values. More specifically, the luminance of the pattern light of the first lighting unit 14A is set to a relatively high first luminance value corresponding to the above "background area" that is a "dark portion". The luminance of the pattern light of the second lighting unit 14B is, on the other hand, set to a second luminance value that is lower than the first luminance value, corresponding to the above "solder printed area" that is a "bright portion".

The third lighting unit 14C and the fourth lighting unit 14D are configured to radiate red uniform light having a fixed light intensity over the entire range. Like the foregoing, however, the third lighting unit 14C is configured to radiate red uniform light having the above first luminance value, and the fourth lighting unit 14D is configured to radiate red uniform light having the above second luminance value.

The fifth lighting unit 14E and the sixth lighting unit 14F are configured to radiate green uniform light having a fixed light intensity over the entire range. Like the foregoing, however, the fifth lighting unit 14E is configured to radiate green uniform light having the above first luminance value, and the sixth lighting unit 14F is configured to radiate green uniform light having the above second luminance value.

The seventh lighting unit 14G and the eighth lighting unit 14H are configured to radiate blue uniform light having a fixed light intensity over the entire range. Like the foregoing, however, the seventh lighting unit 14G is configured to radiate blue uniform light having the above first luminance value, and the eighth lighting unit 14H is configured to radiate blue uniform light having the above second luminance value.

The ninth lighting unit 14I is configured to radiate slit light (sheet-like laser beam). According to one or more embodiments, this slight light is used as measurement light for height measurement (warpage measurement) of the printed circuit board 1.

Among the first lighting unit 14A to the ninth lighting unit 14I described above, the first lighting unit 14A to the eighth lighting unit 14H are subjected to changeover control by the control device 16. More specifically, the control device 16 is configured to sequentially change over the first lighting unit 14A to the eighth lighting unit 14H after elapse of each predetermined time in a predetermined sequence and radiate one of the predetermined lights (pattern light or uniform light) at a predetermined timing. The various lights radiated from the first lighting unit 14A to the eighth lighting unit 14H are projected in a predetermined range on a downstream side of the moving direction of the conveyor 13 during measurement (hereinafter referred to as "first imaging range W1") out of the imaging range W of the camera 14 in the X-axis direction.

The ninth lighting unit 14I, on the other hand, continuously radiates the slit light without any interruption during the continuous move of the printed circuit board 1. This slit light is projected in a predetermined range on an upstream side in the moving direction of the conveyor 13 during measurement (hereinafter referred to as "second imaging range W2") out of the imaging range W of the camera 15.

As shown in FIG. 3, the camera 15 is comprised of, for example, an imaging element (image sensor) 17 and a both-sided telecentric optical system 18. The camera 15 has an optical axis 19 that is set along a vertical direction (Z-axis direction). According to one or more embodiments, a CCD image sensor is employed as the imaging element 17.

The camera 15 is also provided with actuators (not shown) to individually move up and down respective four corner portions of the rectangular flat plate-like imaging element 17. This configuration enables the imaging element 17 to be displaced in the vertical direction and also enables the attitude (inclination) of the imaging element 17 to be adjusted. The imaging element 17 is, however, generally kept in a reference attitude (horizontal attitude) along the horizontal direction.

Figure 4:
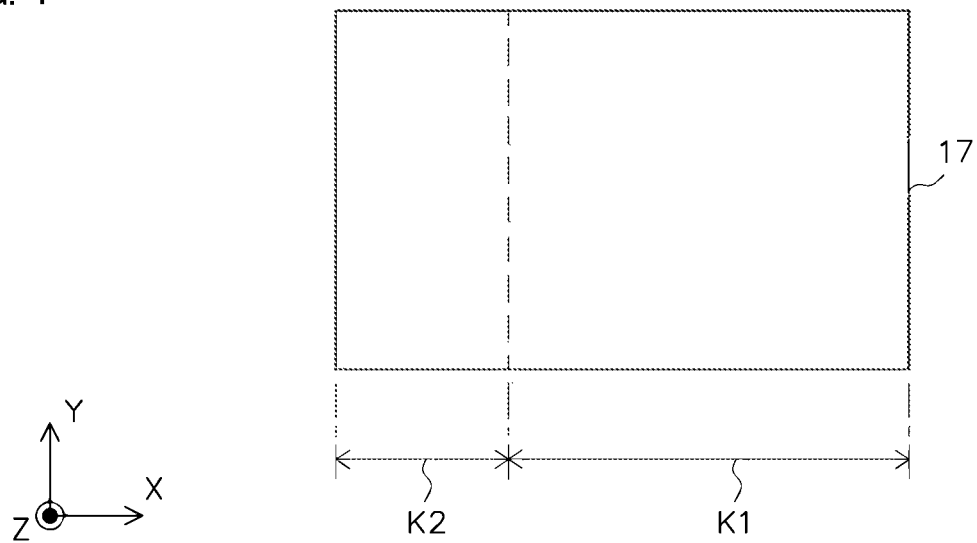
FIG. 4 is a schematic configuration diagram illustrating an imaging element according to one or more embodiments of the present invention.

As shown in FIG. 4, the imaging element 17 is divided into two areas, a first imaging area K1 corresponding to the first imaging range W1 and a second imaging area K2 corresponding to the second imaging range W2. An image in the first imaging range W1 irradiated with the pattern light or the uniform light is taken in the first imaging area K1, and an image in the second imaging range W2 irradiated with the slit light is taken in the second imaging area K2.

The both-sided telecentric optical system 18 is configured by a both-sided telecentric lens integrally including an object-side lens 31, an aperture diaphragm 32, an image-side lens 33 and the like.

The object-side lens 31 serves to condense light reflected from the printed circuit board 1 and has a telecentric structure to make the principal ray parallel to the optical axis 19 on the object side.

The image-side lens 33 serves to cause light transmitted from the object-side lens 31 through the aperture diaphragm 32 to form an image on a light-receiving surface of the imaging element 17 and has a telecentric structure to make the principal ray parallel to the optical axis 19 on the image side.

The aperture diaphragm 32 is placed at the position of a rear-side focal point of the object-side lens 31 and at the position of a front-side focal point of the image-side lens 33.

Image data taken by the camera 15 is converted into a digital signal inside of the camera 15 and is input in the form of the digital signal into the control device 16 to be stored in an image data storage device 24 described later. Image processing, arithmetic operations and the like described later are executed, based on the image data.

The following describes the electrical configuration of the control device 16 in detail with reference to FIG. 5. FIG. 5 is a block diagram illustrating the schematic configuration of the substrate inspection apparatus 10.

As shown in FIG. 5, the control device 16 includes, for example, a CPU and input/output interface 21 configured to control the entire substrate inspection apparatus 10, an input device 22 configured by a keyboard, a mouse, a touch panel and the like as the "input unit", a display device 23 configured as the "display unit" including a display screen such as a CRT or a liquid crystal screen, an image data storage device 24 configured to store, for example, image data taken by the camera 15, and an arithmetic operation result storage device 25 configured to store results of various arithmetic operations, such as results of three-dimensional measurement obtained based on the image data. These respective devices 22 to 25 are electrically connected with the CPU and input/output interface 21.

The image data storage device 24 includes a first data storage area corresponding to the first imaging area K1 of the imaging element 17 and a second data storage area corresponding to the second imaging area K2.

The following describes in detail various processes such as a three-dimensional measurement process executed by the substrate inspection apparatus 10.

At start of measurement with regard to the predetermined range V in the Y-axis direction of the printed circuit board 1, the control device 16 drives and controls the conveyor 13 to continuously move the printed circuit board 1 at a fixed speed. The control device 16 also drives and controls the illumination device 14 and the camera 15, in response to a signal from a non-illustrated encoder provided on the conveyor 13.

Every time the printed circuit board 1 is moved by a predetermined amount Δx, i.e., whenever a predetermined time Δt elapses, an imaging process is executed using the camera 15. According to one or more embodiments, the predetermined amount Δx is set to a distance corresponding to a phase π/8 aliquot (22.5 degrees aliquot) of the pattern light radiated from the first lighting unit 14A and from the second lighting unit 14B. The first imaging range W1 of the camera 15 is set to a length corresponding to a phase 2π aliquot (360 degrees aliquot) of the pattern light.

A process of adjusting the height and the inclination of the imaging element 17 according to the height and the inclination of a predetermined area on the printed circuit board 1 that is an object of a next imaging process is executed between termination of a certain imaging process and start of the next imaging process. The details of this adjustment process of the imaging element 17 will be described later.

Image data taken by the camera 15 (the first imaging area K1 and the second imaging area K2 of the imaging element 17) after elapse of every predetermined time Δt are occasionally transferred to and stored into the image data storage device 24 (the first data storage area and the second data storage area).

More specifically, every time the printed circuit board 1 is moved by the predetermined amount Δx, i.e., whenever the predetermined time Δt elapses, the lights radiated from the first lighting device 14A to the eighth lighting device 14H are changed over in a predetermined sequence, such that one of the lights is projected in the first imaging range W1 of the camera 15. An image of this projected light is taken by the camera 15 (the first imaging area K1 of the imaging element 17) and is stored into the image data storage device 24 (the first data storage area).

Simultaneously, the slit light radiated from the ninth lighting device 14I is projected in the second imaging range W2 of the camera 15. An image of this projected light is taken by the camera 15 (the second imaging area K2 of the imaging element 17) and is stored into the image data storage device 24 (the second data storage area).

When the imaging element 17 is inclined by the adjustment process of the imaging element 17, however, the image data taken by the camera 15 (the first imaging area K1 and the second imaging area K2 of the imaging element 17) are subjected to a predetermined correction process, and corrected image data are stored into the image data storage device 24 (the first data storage area and the second data storage area). The details of this correction process of image data will be described later.

The control device 16 appropriately executes three-dimensional measurement by the phase shift method or measurement using a luminance image, based on the image data stored in the first data storage area of the image data storage device 24 (image data of the first imaging range W1), and executes height measurement (warpage measurement) of the printed circuit board 1, based on the image data stored in the second data storage area of the image data storage device 24 (image data of the second imaging range W2).

The height measurement (warpage measurement) of the printed circuit board 1 is described first. This height measurement is executed by a known light section method using the slit light and is sequentially executed every time image data is newly stored into the second data storage area of the image data storage device 24 (i.e., whenever the predetermined time Δt elapses).

The control device 16 calculates an amount of deviation between the position of the slit light projected on the printed circuit board 1 and a predetermined reference position (for example, a projected position of the slit light when the printed circuit board has no warpage), based on the image data stored in the second data storage area of the image data storage device 24. When the height position at a predetermined coordinate position of the printed circuit board 1 is different from a reference height position, the position of the slit light projected in the second imaging range W2 of the camera 15 is deviated in the X-axis direction.

The control device 16 subsequently calculates an amount of deviation in the Z-axis direction (height direction) of the height position from the reference height position at each coordinate position of the printed circuit board 1, based on the principle of triangulation, and stores the calculated amount of deviation as relative height data at the coordinate position on the printed circuit board 1 into the arithmetic operation result storage device 25.

In this manner, every time the printed circuit board 1 is moved by the predetermined amount Δx, the projected position of the slit light is relatively moved, and height data at the respective coordinate positions on the printed circuit board 1 are sequentially stored.

The inclination of a predetermined area on the printed circuit board 1 may also be calculated by determining the height data at the respective coordinate positions on the printed circuit board 1. According to one or more embodiments, the measurement unit is thus implemented by the functions of the ninth lighting unit 14I configured to radiate the slit light, the camera 15 (second imaging area K2 of the imaging element 17) configured to take an image of the slit light, the image data storage device 24 (second data storage area) configured to store the taken image data, and the control device 16 configured to execute height measurement (including inclination measurement) of the printed circuit board 1.

The following describes in detail the adjustment process of the imaging element 17 executed between termination of a certain imaging process and start of a next imaging process.

The control device 16 first extracts height data at each coordinate position in a predetermined area on the printed circuit board that is an object of a subsequent imaging process (a predetermined area on the prince circuit board 1 that is located in the imaging range W at a next imaging timing), based on the result of the height measurement described above (height data at each coordinate position on the printed circuit board 1).

Figure 6:
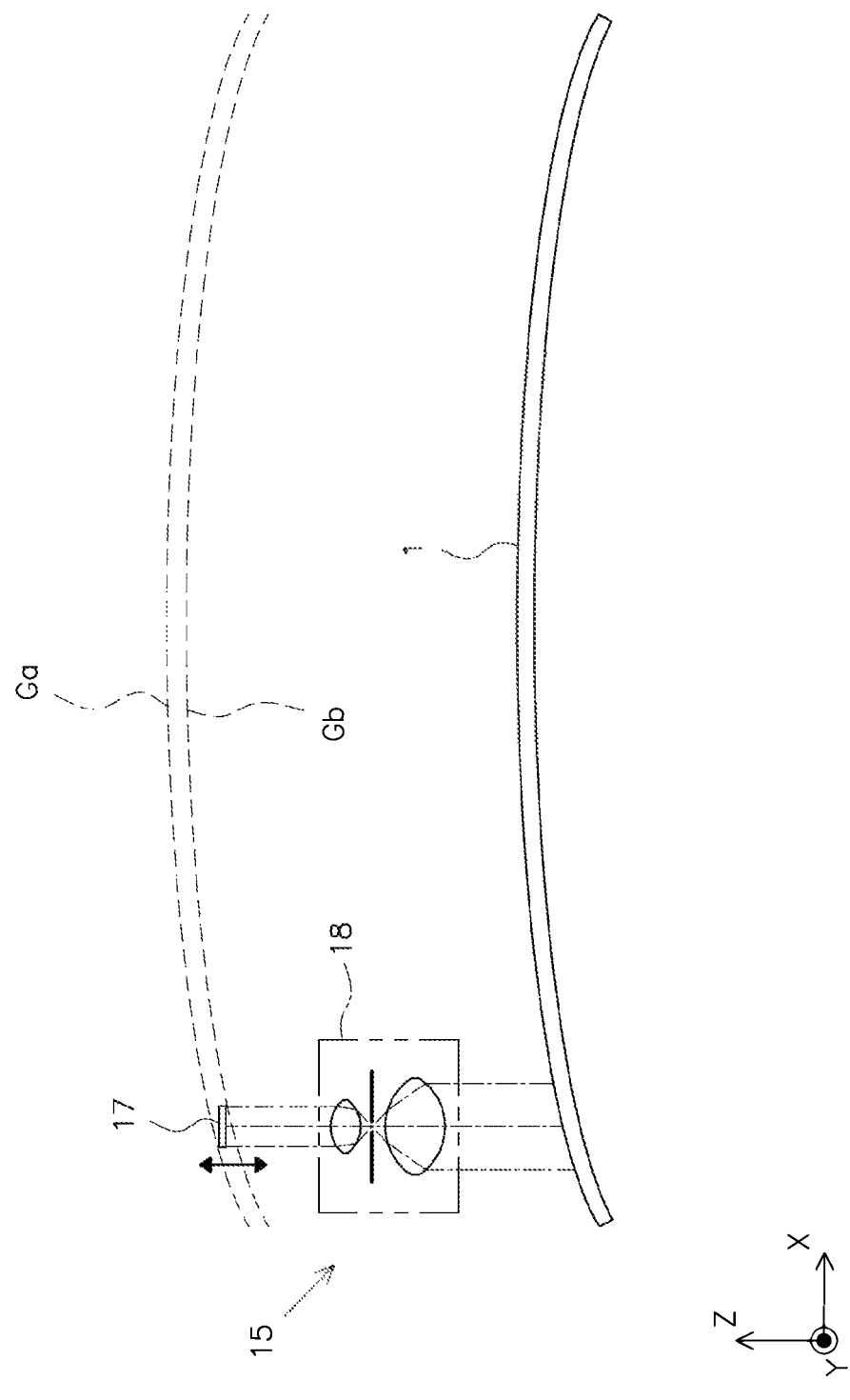
FIG. 6 is a diagram illustrating a relationship between warpage of the printed circuit board and a focusing range according to one or more embodiments of the present invention.

The control device 16 subsequently adjusts the height position of the imaging element 17, such that a height difference between the height at a predetermined coordinate position on the printed circuit board 1 that intersects with the optical axis 19 of the camera 15 at a next imaging timing and the height at a center position of the imaging element 17 becomes equal to a set value determined in advance (predetermined distance) (as shown in FIG. 6). FIG. 6 is a diagram illustrating a relationship between warpage of the printed circuit board 1 and a focusing range. According to one or more embodiments, the set value is determined, such that the center position of the imaging element 17 is located in the middle of an upper limit Ga of the focusing range and a lower limit Gb of the focusing range relative to the printed circuit board 1.

Figure 7:
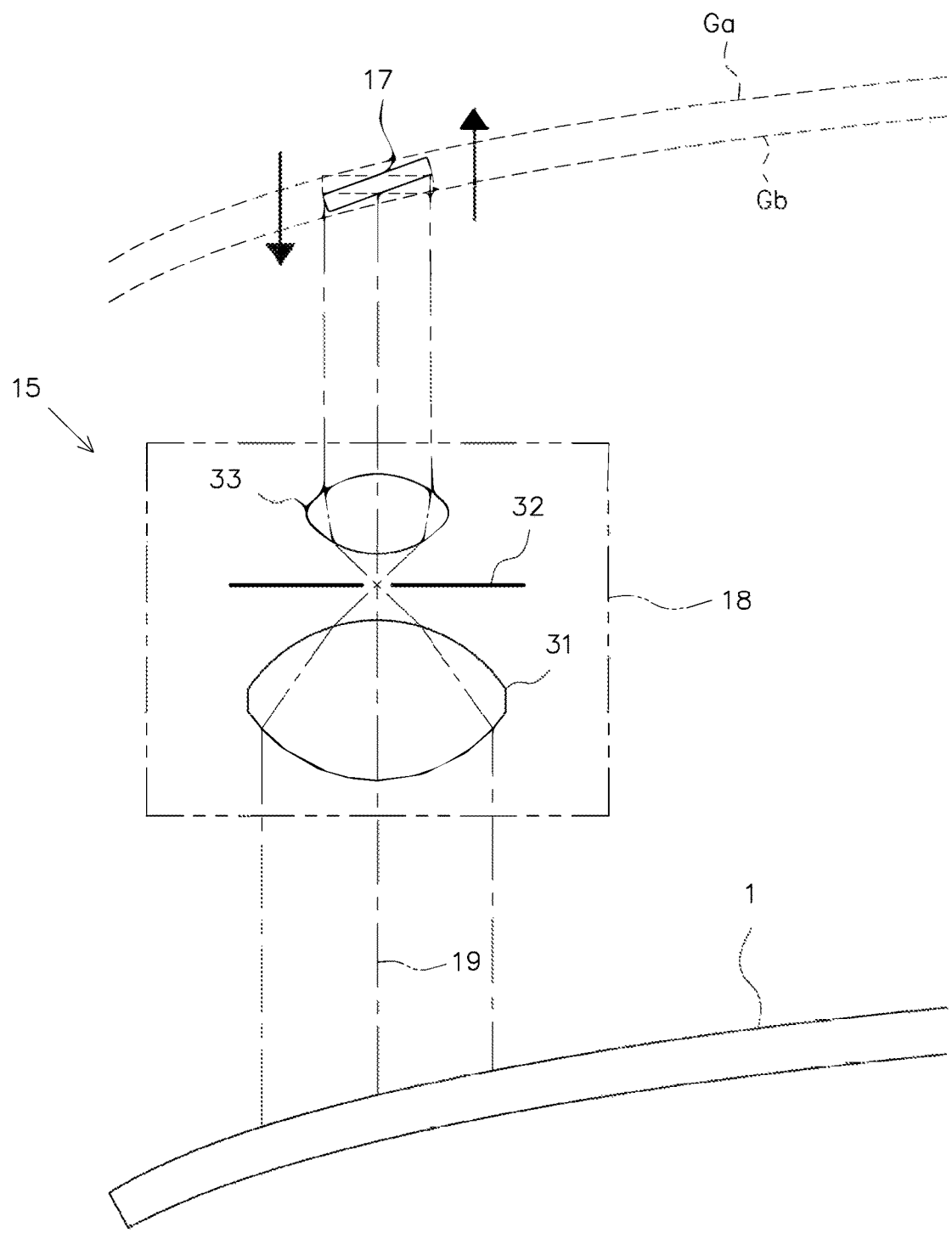
FIG. 7 is a diagram illustrating inclination adjustment of the imaging element according to one or more embodiments of the present invention.

The control device 16 then adjusts the inclination of the imaging element 17, such that the inclination of the imaging element 17 corresponds to the inclination of the predetermined area on the printed circuit board 1 that is the object of the next imaging process (as shown in FIG. 7). More specifically, the inclination of the imaging element 17 is adjusted, such that a height difference between the height at each coordinate position in the predetermined area on the printed circuit board 1 and the height of each pixel of the imaging element 17 corresponding to the coordinate position becomes equal to the above set value determined in advance.

After completion of the height adjustment and the inclination adjustment, an imaging process is executed with regard to the predetermined area on the printed circuit board 1 at a predetermined timing. According to one or more embodiments, the adjustment unit is thus implemented by the functions of the actuators configured to displace the imaging element 17 and the control device 16 configured to control the actuators and execute the height adjustment and the inclination adjustment.

The correction process of image data executed in the inclination adjustment of the imaging element 17 is described in detail. In particular, when the imaging element 17 is inclined, the concrete process concretes a deviation of image data caused by the positional deviation of each pixel in the horizontal direction (deviation of a positional relationship between each pixel of the imaging element 17 and the corresponding coordinate position on the printed circuit board 1). According to one or more embodiments, the correction unit is implemented by the functions of this correction process.

Figures 8A, 8B:
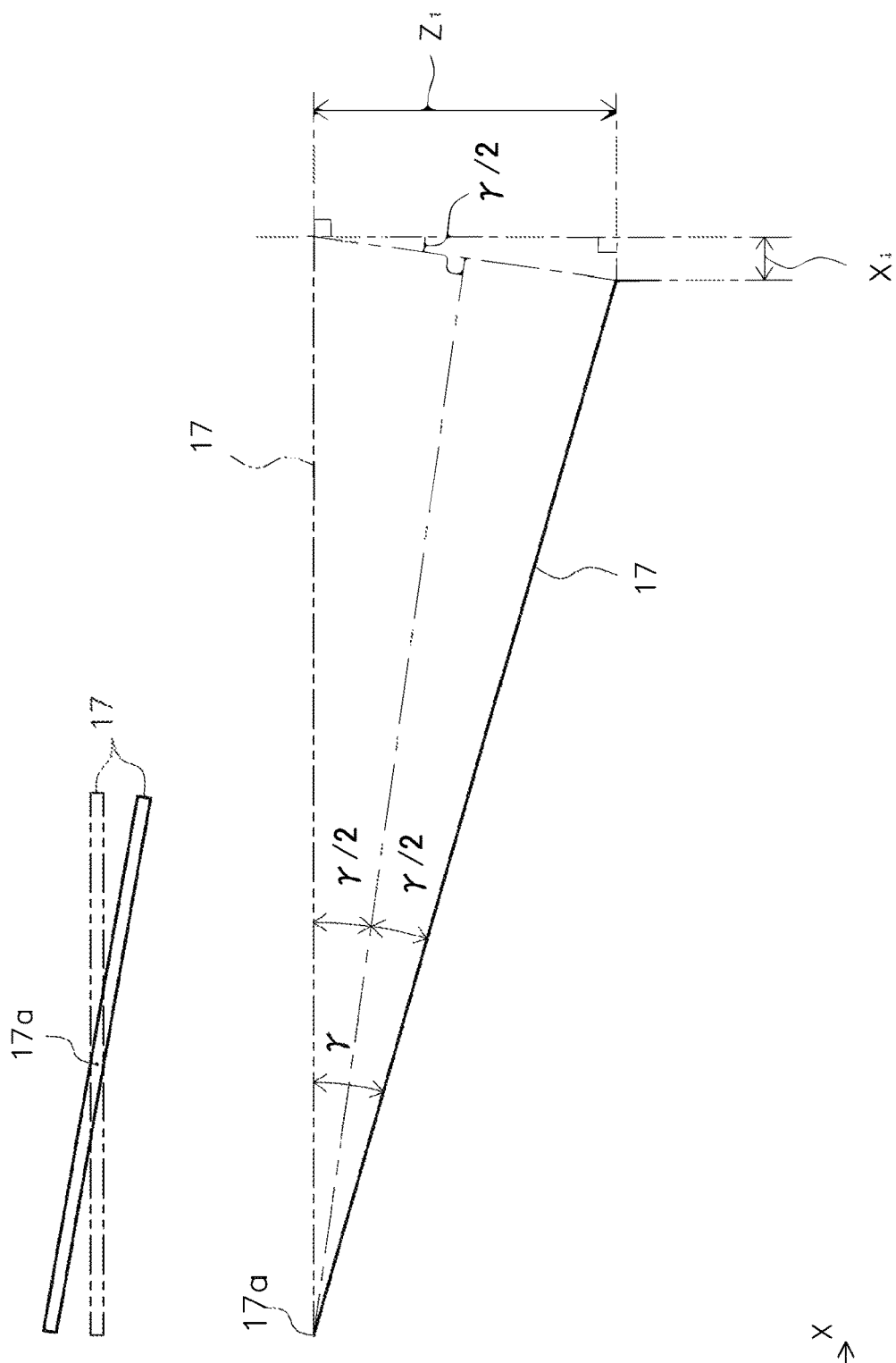
FIG. 8A is a diagram illustrating the imaging element that is inclined relative to a reference attitude.
FIG. 8B is a diagram illustrating correction of a horizontal deviation of image data according to one or more embodiments of the present invention.

For example, as shown in FIGS. 8A and 8B, when the imaging element 17 in the reference attitude (horizontal attitude) is inclined by γ relative to the Y-axis direction of an X-axis direction middle portion 17a as the axial center, an amount of horizontal deviation $X_1$ at one end in the X-axis direction may be derived by Expression (a) given below:

$$X_1 = Z_1 \tan(\gamma/2) \quad \text{(a)}$$

where $Z_1$ denotes a height difference between one end in the X-axis direction and the middle portion 17a (half a height difference between respective ends in the X-axis direction).

For example, when γ=1 degree and $Z_1$=0.5 mm (the height difference between the respective ends in the X-axis direction is 1 mm), tan(γ/2)=0.0087, so that a pixel at one end in the X-axis direction has the amount of horizontal deviation $X_1$=4 μm.

This amount of horizontal deviation may be determined by calculation each time or may be determined based on a numerical table or table data that is prepared in advance and indicates a correspondence relationship between the imaging element 17 and the inclination angle. The operation expression used to calculate the amount of horizontal deviation $X_1$ is not limited to Expression (a) given above but may be another operation expression.

The following describes in detail a relationship between the lights radiated from the first lighting unit 14A to the eighth lighting unit 14H of the illumination device 14 and the printed circuit board 1 imaged in the first imaging range W1 of the camera 15 (the first imaging area K1 of the imaging element 17).

Figure 9:
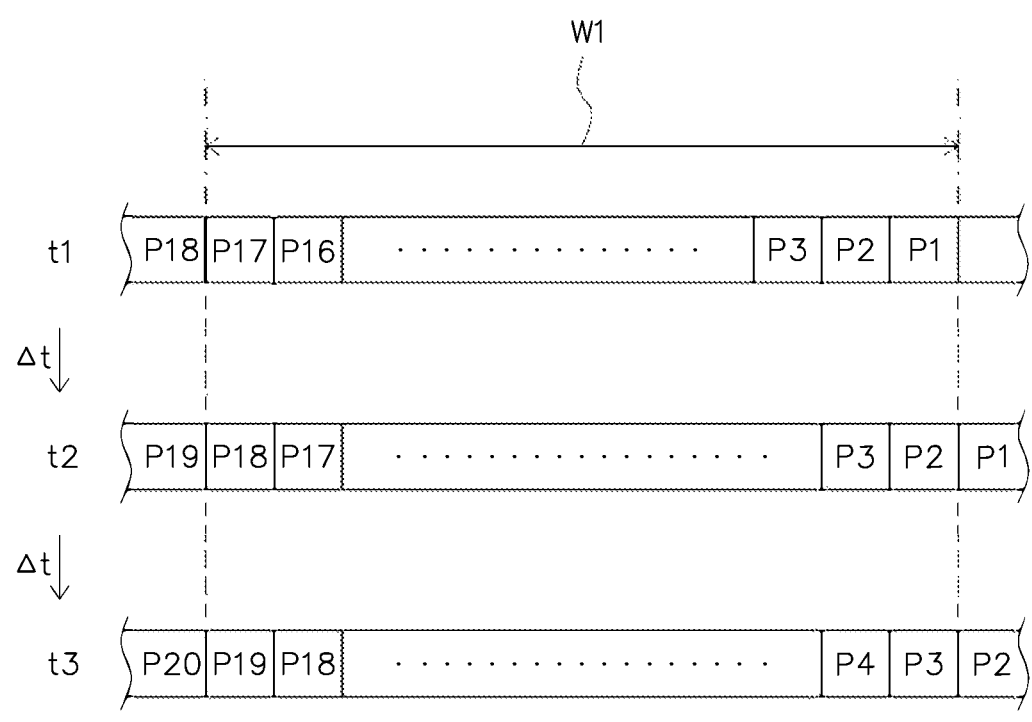
FIG. 9 is a diagram illustrating a relationship between an imaging range of the camera that changes with elapse of time and coordinate positions on the printed circuit board according to one or more embodiments of the present invention.

FIG. 9 is a diagram illustrating a relationship between the first imaging range W1 of the camera 15 that relatively moves with elapse of time and coordinate positions on the printed circuit board 1. FIGS. 10A, 10B are correspondence tables illustrating types of irradiation lights that change with elapse of time and specifications of the irradiation lights (for example, the phase of the pattern light and the color of the uniform light) at respective coordinate positions on the printed circuit board 1.

As shown in FIG. 9 and FIGS. 10A, 10B at a predetermined imaging timing t1, the printed circuit board 1 is irradiated with the pattern light of the first luminance value from the first lighting unit 14A. At this moment, a range corresponding to coordinates P1 to P17 in its moving direction (X-axis direction) of the printed circuit board 1 is located in the first imaging range W1 of the camera 15.

In other words, at the imaging timing t1, the range of the coordinates P1 to P17 on the surface of the printed circuit board 1 irradiated with the pattern light of the first luminance value is imaged by the first imaging area K1 of the imaging element 17. More specifically, image data of the printed circuit board 1 irradiated with the pattern light are obtained by shifting the phase of the pattern light by every "22.5 degrees" at each of the coordinates P1 to P17, for example, "0 degree" at the coordinate P17, "22.5 degrees" at the coordinate P16, "45 degrees" at the coordinate P15, ..., "360 degrees" at the coordinate P1.

At an imaging timing t2 after elapse of the predetermined time Δt since the imaging timing t1, the printed circuit board 1 is irradiated with the red uniform light of the first luminance value from the third lighting unit 14C. At this moment, a range corresponding to coordinates P2 to P18 of the printed circuit hoard 1 is located in the first imaging range W1 of the camera 15, and this range is imaged by the first imaging area K1 of the imaging element 17. A symbol "R1" at each coordinate position in FIGS. 10A, 10B indicates that the radiated at the position is the "red uniform light of the first luminance value".

At an imaging timing t3 after elapse of the predetermined time Δt since the imaging timing t2, the printed circuit board 1 is irradiated with the pattern light of the second luminance value from the second lighting unit 14B. At this moment, a range corresponding to coordinates P3 to P19 of the printed circuit board 1 is located in the first imaging range W1 of the camera 15, and this range is imaged by the first imaging area K1 of the imaging element 17.

At an imaging timing t4 after elapse of the predetermined time Δt since the imaging timing t3, the printed circuit board 1 is irradiated with the red uniform light of the second luminance value from the fourth lighting unit 14D. At this moment, a range corresponding to coordinates P4 to P20 of the printed circuit board 1 is located in the first imaging range W1 of the camera 15, and this range is imaged by the first imaging area K1 of the imaging element 17, A symbol "R2" at each coordinate position in FIGS. 10A, 10B indicates that the light radiated at the position is the "red uniform light of the second luminance value".

At an imaging timing t5 after elapse of the predetermined time Δt since the imaging timing t4, the printed circuit board 1 is irradiated with the pattern light of the first luminance value from the first lighting unit 14A. At this moment, a range corresponding to coordinates P5 to P21 of the printed circuit board 1 is located in the first imaging range W1 of the camera 15, and this range is imaged by the first imaging area K1 of the imaging element 17.

At an imaging timing t6 after elapse of the predetermined time Δt since the imaging timing t5, the printed circuit board 1 is irradiated with the green uniform light of the first luminance value from the fifth lighting unit 14E. At this moment, a range corresponding to coordinates P6 to P22 of the printed circuit board 1 is located in the first imaging range W1 of the camera 15, and this range is imaged by the first imaging area K1 of the imaging element 17. A symbol "G1" at each coordinate position in FIGS. 10A, 10B indicates that the light radiated at the position is the "green uniform light of the first luminance value".

At an imaging timing t7 after elapse of the predetermined time Δt since the imaging timing t6, the printed circuit board 1 is irradiated with the pattern light of the second luminance value from the second lighting unit 14B. At this moment, a range corresponding to coordinates P7 to P23 of the printed circuit board 1 is located in the first imaging range W1 of the camera 15, and this range is imaged by the first imaging area K1 of the imaging element 17.

At an imaging timing t8 after elapse of the predetermined time Δt since the imaging timing t7, the printed circuit board 1 is irradiated with the green uniform light of the second luminance value from the sixth lighting unit 14F. At this moment, a range corresponding to coordinates P8 to P24 of the printed circuit board 1 is located in the first imaging range W1 of the camera 15, and this range is imaged by the first imaging area K1 of the imaging element 17. A symbol "G2" at each coordinate position in FIGS. 10A, 10B indicates that the light radiated at the position is the "green uniform light of the second luminance value".

At an imaging timing t9 after elapse of the predetermined time Δt since the imaging timing t8, the printed circuit board 1 is irradiated with the pattern light of the first luminance value from the first lighting unit 14A. At this moment, a range corresponding to coordinates P9 to P25 of the printed circuit board 1 is located in the first imaging range W1 of the camera 15, and this range is imaged by the first imaging area K1 of the imaging element 17.

At an imaging timing t10 after elapse of the predetermined time Δt since the imaging timing t9, the printed circuit board 1 is irradiated with the blue uniform light of the first luminance value from the seventh lighting unit 14G. At this moment, a range corresponding to coordinates P10 to P26 of the printed circuit board 1 is located in the first imaging range W1 of the camera 15, and this range is imaged by the first imaging area K1 of the imaging element 17. A symbol "B1" at each coordinate position in FIGS. 10A, 10B indicates that the light radiated at the position is the "blue uniform light of the first luminance value".

At an imaging timing t11 after elapse of the predetermined time Δt since the imaging timing t10, the printed circuit board 1 is irradiated with the pattern light of the second luminance value from the second lighting unit 14B. At this moment, a range corresponding to coordinates P11 to P27 of the printed circuit board 1 is located in the first imaging range W1 of the camera 15, and this range is imaged by the first imaging area K1 of the imaging element 17.

At an imaging timing t12 after elapse of the predetermined time Δt since the imaging timing t11, the printed circuit board 1 is irradiated with the blue uniform light of the second luminance value from the eighth lighting unit 14H. At this moment, a range corresponding to coordinates P12 to P28 of the printed circuit board 1 is located in the first imaging range W1 of the camera 15, and this range is imaged by the first imaging area K1 of the imaging element 17. A symbol "B2" at each coordinate position in FIGS. 10A, 10B indicates that the light radiated at the position is the "blue uniform light of the second luminance value".

At an imaging timing t13 after elapse of the predetermined time Δt since the imaging timing t12, the printed circuit board 1 is irradiated with the pattern light of the first luminance value from the first lighting unit 14A. At this moment, a range corresponding to coordinates P13 to P29 of the printed circuit board 1 is located in the first imaging range W1 of the camera 15, and this range is imaged by the first imaging area K1 of the imaging element 17.

At an imaging timing t14 after elapse of the predetermined time Δt since the imaging timing t13, no light is radiated from any of the first lighting unit 14A to the eighth lighting unit 14H. The imaging process by the camera 15 is, however, executed normally to take an image of the slit light radiated from the ninth lighting unit 14I.

At an imaging timing t15 after elapse of the predetermined time Δt since the imaging timing t14, the printed circuit board 1 is irradiated with the pattern light of the second luminance value from the second lighting unit 14B. At this moment, a range corresponding to coordinates P15 to P31 of the printed circuit board 1 is located in the first imaging range W1 of the camera 15, and this range is imaged by the first imaging area K1 of the imaging element 17.

At an imaging timing t16 after elapse of the predetermined time Δt since the imaging timing t15, no light is radiated from any of the first lighting unit 14A to the eighth lighting unit 14H. The imaging process by the camera 15 is, however, executed normally to take an image of the slit light radiated from the ninth lighting unit 14I.

At an imaging timing after elapse of the predetermined time Δt since the imaging timing t16, a process similar to the process at the imaging timing t1 described above is executed. Subsequently, processes similar to the processes at the imaging timings t1 to t16 are executed repeatedly.

After all the data are obtained with regard to a predetermined coordinate position (for example, coordinate P17) of the printed circuit board 1 in the above manner, a position adjustment process is executed to adjust the coordinate positions of the respective image data (adjust the coordinate systems of the respective image data) (as shown in FIGS. 11A, 11B). FIGS. 11A, 11B are tables schematically illustrating the state of position adjustment of the coordinate positions with regard to a plurality of image data obtained at the imaging timings t1 to t16.

Various data with regard to identical coordinate positions among the plurality of image data are collected for each coordinate position, are organized in respective preset groups (categories), and are stored in the arithmetic operation result storage device 25 (as shown in FIGS. 12A, 12B). FIGS. 12A, 12B are tables schematically illustrating various data with regard to the respective coordinate positions of the printed circuit board 1 shown in FIGS. 11A, 11B, which are organized in the respective preset groups and are rearranged. FIGS. 12A, 12B illustrate only data part with regard to the coordinate P17 of the printed circuit board 1.

According to one or more embodiments, various data are classified and stored in four group data with regard to each coordinate position of the printed circuit board 1; first group data that are obtained by imaging under the pattern light of the first luminance value and that are comprised of four different data having the phases of the pattern light shifted by 90 degrees each; second group data that are obtained by imaging under the pattern light of the second luminance value and that are comprised of four different data having the phases of the pattern light shifted by 90 degrees each; third group data that are obtained by imaging under the uniform lights of the respective color components, red, green and blue, of the first luminance value and that are comprised of luminance data of the three color components; and fourth group data that are obtained by imaging under the uniform lights of the respective color components, red, green and blue, of the second luminance value and that are comprised of luminance data of the three color components.

The control device 16 subsequently executes various processes corresponding to the respective groups, based on the respective group data described above.

More specifically, the control device 16 executes three-dimensional measurement at each coordinate by the known phase shift method described in Background, based on the first group data. Three-dimensional data of the entire printed circuit board 1 (hereinafter referred to as first three-dimensional data) are calculated by repeating this process with regard to the respective coordinates and are stored in the arithmetic operation result storage device 25.

The control device 16 similarly executes three-dimensional measurement at each coordinate by the known phase shift method, based on the second group data. Three-dimensional data of the entire printed circuit board 1 (hereinafter referred to as second three-dimensional data) are calculated by repeating this process with regard to the respective coordinates and are stored in the arithmetic operation result storage device 25.

According to one or more embodiments, the image processing unit (three-dimensional measurement unit) is implemented by the function of calculating the three-dimensional data of the printed circuit board 1 by the phase shift method.

The control device 16 also generates color image data of the entire printed circuit board 1 having the respective color components, red, green and blue (hereinafter referred to as first color image data), based on the third group data and are stored in the arithmetic operation result storage device 25.

The control device 16 similarly generates color image data of the entire printed circuit board 1 having the respective color components, red, green and blue (hereinafter referred to as second color image data), based on the fourth group data and are stored in the arithmetic operation result storage device 25.

The control device 16 subsequently distinguishes the color information of the respective pixels of the above respective color image data and extracts respective measurement object areas. For example, the control device 16 extracts a range of "white" pixels from the second color image data as a solder printed area, extracts a range of "red" pixels from the first color image data as an electrode area (background area) where the electrode pattern 3 is exposed, and extracts a range of "green" pixels as a substrate area (background area) where the base substrate 2 or the resist film 5 is exposed.

The control device 16 then determines the good/poor quality of the printed state of the solder paste 4, based on the measurement results obtained as described above. More specifically, the control device 16 detects a printing range of the solder paste 4 that is higher by a predetermined length or more than a height reference surface and calculates a volume of a location in the detected range. The control device 16 subsequently compares the calculated volume with a preset reference value and determines the good/poor quality of the printed state of the solder paste 4 based on determination of whether the result of this comparison is within an allowable range.

In this determination process, one or more embodiments of the present invention employ the value of the first three-dimensional data with regard to the solder printed area extracted from the second color image data and employ the value of the second three-dimensional data with regard to the background area that serves as the height reference surface.

As described above in detail, for the purpose of three-dimensional measurement by the phase shift method, the configuration of one or more embodiments irradiates the continuously moving printed circuit board 1 with the pattern light having the striped light intensity distribution and takes an image of the printed circuit board 1 with the camera 15 every time the printed circuit board 1 irradiated with the pattern light is moved by the predetermined amount. This configuration obtains four different image data having the phases of the radiated pattern light shifted by 90 degrees each. Three-dimensional measurement of, for example, the solder paste 4 is then executed, based on these image data.

The configuration of one or more embodiments takes images with adjusting the height position and the inclination of the imaging element 17 corresponding to the predetermined area (imaging area) on the printed circuit board 1 and thereby enables focused images to be obtained constantly. As a result, even when the printed circuit board 1 has a warpage or the like, this configuration enables the entire printed circuit board 1 to be placed in the focusing range (i.e., enables a focused image to be obtained with regard to the entire printed circuit board 1) and thereby improves the measurement accuracy.

Especially, the configuration of the embodiment executes the height adjustment and the inclination adjustment by displacing only the imaging element 17. This achieves significant downsizing of the mechanism involved in the height adjustment and the inclination adjustment. This configuration also allows for minute and quick movements and thus significantly improves the measurement accuracy and the measurement speed.

Additionally, the configuration of one or more embodiments executes the height adjustment and the inclination adjustment by utilizing the both-sided telecentric optical system. This reduces the effect on the magnification caused by, for example, a position change of the imaging element 17 and a height change of the surface of the printed circuit board 1.

Furthermore, the configuration of one or more embodiments corrects the deviation of the image data caused by the positional deviation of each pixel in the horizontal direction in the case of inclination of the imaging element 17 by the software-based arithmetic operation and thus suppresses reduction of the measurement accuracy.

Especially, the configuration of one or more embodiments uses the both-sided telecentric optical system 18 and causes the imaging element 17 to receive the light that is parallel to the optical axis 19. Accordingly, by obtaining the amount of inclination of the imaging element 17, the amount of horizontal deviation of each pixel can be determined accurately according to a simple computation expression. This configuration thus readily provides the correspondence relationship of each pixel of the imaging element 17 to the coordinate position on the printed circuit board 1. As a result, this reduces the load of the control process.

The configuration of one or more embodiments takes an image of the second imaging range W2 irradiated with the slit light by the second imaging area K2 located on the upstream side (left side in FIG. 1) in the X-axis direction of the camera 15 (imaging element 17) and executes height measurement (warpage measurement) of the printed circuit board 1, while continuously moving the printed circuit board 1. The configuration of one or more embodiments also take an image of the first imaging range W1 irradiated with the pattern light by the first imaging area K1 located on the downstream side (right side in FIG. 1) in the X-axis direction and executes three-dimensional measurement of the solder paste 4 or the like.

This configuration accordingly allows for imaging for the purpose of three-dimensional measurement of the solder paste 4 or the like with adjusting the imaging element 17 into the focusing range, while continuously moving the printed circuit board 1. This improves the measurement efficiency. Moreover, the configuration of one or more embodiments enables three-dimensional measurement of the entire printed circuit board 1 to be executed by continuously moving the printed circuit board 1 only in one direction without requiring reciprocation of the printed circuit board 1, according to the relationship between the width of the printed circuit board 1 and the imaging range of the camera 15 in the Y-axis direction. Furthermore, the configuration of one or more embodiments enables both imaging for height measurement (warpage measurement) of the printed circuit board 1 and imaging for three-dimensional measurement of the solder paste 4 or the like to be executed simultaneously. This simplifies the imaging process.

The configuration of one or more embodiments executes height measurement (warpage measurement) of the printed circuit board 1 and three-dimensional measurement of the solder paste 4 or the like, based on the image data obtained by the single camera 15 (identical optical system). This configuration improves the position accuracy (i.e., readily matches the image data in the unit of pixels and handles the image data in one identical coordinate system) and achieves downsizing and simplification of the apparatus, compared with a configuration separately provided with a plurality of imaging mechanisms (cameras).

According to one or more embodiments of the present invention, multiple imaging processes under the pattern light of the second luminance value for the purpose of three-dimensional measurement by the phase shift method and imaging processes under the uniform lights of the respective color components of the first luminance value and the second luminance value for the purpose of obtaining the luminance image data are executed in between multiple imaging processes under the pattern light of the first luminance value for the purpose of three-dimensional measurement by the phase shift method.

This configuration accordingly enables image data used for an application other than the three-dimensional measurement to be separately obtained, in addition to image data used for the three-dimensional measurement without extending the time period required to obtain all the image data that are needed for three-dimensional measurement by the phase shift method.

As a result, this configuration allows for combination of a plurality of different types of measurements and improves the measurement accuracy with suppressing reduction of the measurement efficiency in three-dimensional measurement by the phase shift method.

This configuration changes the luminance of the irradiation light and separately executes imaging with the luminance value suitable for the solder printed area (bright portion) and imaging with the luminance value suitable for the background area (dark portion). This suppresses the occurrence of various troubles due to the difference in brightness of respective locations on the printed circuit board 1.

The present disclosure is not limited to the description of the above embodiments but may be implemented, for example, by configurations described below. The present disclosure may also be naturally implemented by applications and modifications other than those illustrated below.

(a) According to the above embodiments, the three-dimensional measurement device is embodied in the substrate inspection apparatus 10 configured to execute three-dimensional measurement of the solder paste 4 printed and formed on the printed circuit board 1. This is, however, not restrictive. For example, the three-dimensional measurement device may be embodied in a configuration of executing three-dimensional measurement of other objects, for example, a solder bump printed on a substrate or an electronic component mounted on a substrate.

(b) According to the above embodiments, four different image data having the phases shifted by 90 degrees each in three-dimensional measurement by the phase shift method. The number of times of phase shift and the amount of phase shift are, however, not restricted to those of the above embodiments. Another number of times of phase shift and another amount of phase shift may be employed in three-dimensional measurement by the phase shift method.

For example, a modified configuration may obtain three different image data having the phases shifted by 120 degrees (or 90 degrees) each and execute three-dimensional measurement. Another modified configuration may obtain two different image data having the phases shifted by 180 degrees (or 90 degrees) each and execute three-dimensional measurement.

(c) The configuration (moving unit) of relatively moving the measurement head 12 (the illumination device 14 and the camera 15) and the printed circuit board 1 is not limited to that of the above embodiments.

For example, according to the above embodiments, on termination of measurement of the entire range in the X-axis direction with regard to the predetermined range V in the Y-axis direction of the printed circuit board 1 with continuously moving the printed circuit board 1 rightward in the X-axis direction by the conveyor 13, the configuration of the above embodiments moves the printed circuit board 1 in the opposite direction (leftward in the X-axis direction) to return the printed circuit board 1 to its initial position, and moves the measurement head 12 by the predetermined amount along the Y-axis direction. The configuration of the above embodiments then executes again measurement of the entire range in the X-axis direction of the printed circuit board 1 with continuously moving the printed circuit board 1 rightward in the X-axis direction.

This configuration is, however, not restrictive. A modified configuration may fix the measurement head 12 to be unmovable and may be provided with a stage which the printed circuit board 1 is placed on and a driving unit that moves the stage both in the X-axis direction and in the Y-axis direction, so as to relatively move the measurement head 12 and the printed circuit board 1.

Another modified configuration may, on the contrary, fix the printed circuit board 1 to be unmovable and may be provided with the measurement head 12 that is movable both in the X-axis direction and in the Y-axis direction, so as to relatively move the measurement head 12 and the printed circuit board 1.

Another modified configuration may execute various measurements without relatively moving but stopping the measurement head 12 and the printed circuit board 1. For example, this modified configuration may intermittently move the printed circuit board 1 and sequentially stop predetermined ranges on the printed circuit board 1 in the imaging range of the camera 15 to execute various measurements.

(d) The configuration relating to the irradiation unit, for example, the types of lights radiated from the respective lighting units, is not limited to the illumination device 14 of the above embodiments.

For example, the configuration of the above embodiments is provided with the plurality of uniform light lighting units that radiate the uniform lights, for example, the third lighting unit 14C, as well as the first lighting unit 14A and the second lighting unit 14B that radiate the pattern lights. This configuration is, however, not restrictive. A modified configuration may be provided with only the first lighting unit 14A and the second lighting unit 14B to obtain only the image data required for three-dimensional measurement by the phase shift method. The modified configuration may be provided with only either one of the first lighting unit 14A and the second lighting unit 14B.

(e) The configuration of the above embodiments irradiates the printed circuit board 1 with the slit light from the ninth lighting unit 14I and executes height measurement (including inclination measurement) of the printed circuit board 1 by the known light section method, based on the image data obtained by imaging the slit light with the camera 15.

The configuration involved in height measurement of the printed circuit board 1 is, however, not limited to this example of the embodiments. For example, another measurement technique different from the light section method may be employed for height measurement, for example, radiation of a laser pointer from the ninth lighting unit 14I or radiation of pattern light having a broader cycle of stripes than the pattern light radiated from the first lighting unit 14A or the like (i.e., the pattern light for three-dimensional measurement of the solder paste 4 or the like). In order not to decrease the measurement efficiency, however, a measurement technique that relatively readily determines the height while continuously moving the printed circuit board 1 at a high speed, such as the light section method, is employed according to one or more embodiments of the present invention.

(f) The configuration of the above embodiments irradiates the printed circuit board 1 with the striped pattern lights from the first lighting unit 14A and the second lighting unit 14B and executes three-dimensional measurement of the solder paste 4 or the like by the phase shift method. This configuration is, however, not restrictive. A modification may employ another three-dimensional measurement method, for example, a space code method or a moire method. However, a measurement method of high measurement accuracy, for example, phase shift method is employed, for measurement of a small measurement object such as the solder paste 4, according to one or more embodiments of the present invention.

(g) The configuration of the above embodiments executes height measurement of the printed circuit board by causing the second imaging area K2 located on the upstream side (left side in FIG. 1) in the X-axis direction of the camera 15 (the imaging element 17) to take an image of the second imaging range W2 irradiated with the slit light, while continuously moving the printed circuit board 1. The configuration of the above embodiments also executes three-dimensional measurement of the solder paste 4 or the like by causing the first imaging area K1 located on the downstream side (right side in FIG. 1) in the X-axis direction to take an image of the first imaging range W1 irradiated with the pattern light.

This configuration is, however, not restrictive. Another configuration may be employed to execute height measurement of a predetermined area on the printed circuit board 1 in at least a stage prior to imaging of the predetermined area for the purpose of three-dimensional measurement by the phase shift method.

For example, while reciprocating the printed circuit board 1, a modified configuration may execute height measurement (warpage measurement) of the printed circuit board 1 at a high speed by radiation of only the slit light in its forward path, and may execute imaging in its backward path for the purpose of three-dimensional measurement of the solder paste 4 with adjusting the imaging element 17 to the focusing range based on the result of the height measurement.

Another modified configuration may provide an irradiation unit and an imaging unit used for height measurement of the printed circuit board 1, separately from the irradiation unit and the imaging unit (the illumination device 14 and the camera 15) used for three-dimensional measurement by the phase shift method.

(h) Although not being specifically described in the above embodiments, height measurement (warpage measurement) of the printed circuit board 1 may measure the heights of the base substrate 2 and the electrode pattern 3 of the printed circuit board 1 or may measure the height of the entire printed circuit board 1 including the solder paste 4.

However, not only the heights of the base substrate 2 and the electrode pattern 3 of the printed circuit board 1 but the height of the entire printed circuit board 1 including the solder paste 4 are measured according to one or more embodiments of the present invention. This allows for subsequent adjustment of the imaging element 17 by taking into account the upper limit Ga of the focusing range.

(i) The configuration of the above embodiments calculates the amount of deviation in the Z-axis direction (height direction) from the reference height position at each coordinate position on the printed circuit board 1 and stores the calculated amount of deviation, as relative height data of each coordinate position on the printed circuit board 1, into the arithmetic operation result storage device 25.

This configuration is, however, not restrictive. A modified configuration of height measurement of the printed circuit board 1 may measure the absolute height of the printed circuit board 1. Another modified configuration of height measurement of the printed circuit board 1 may measure the relative height of the printed circuit board 1 to a predetermined reference (for example, the both-sided telecentric optical system 18 of the camera 15).

(j) When height measurement (warpage measurement) of the printed circuit board 1 is allowed at the resolution over a predetermined resolving power, this may be used as information for identifying the degree in three-dimensional measurement of the solder paste 4 or the like. This allows for expansion of the dynamic range of height in three-dimensional measurement.

(k) The configuration of the above embodiments is provided with the actuators that individually move up and down the respective four corner portions of the imaging element 17. The configuration of executing height adjustment and inclination adjustment of the imaging element 17 is, however, not limited to this example of the embodiments. For example, a modification may be provided with a mechanism that executes inclination adjustment by rotating the imaging element 17 about a predetermined rotating axis and with a mechanism that executes height adjustment by moving up and down the mechanism.

The procedure of height adjustment and inclination adjustment is not limited to that of the above embodiments. For example, the above embodiments successively execute height adjustment and inclination adjustment. A modification may, however, execute height adjustment and inclination adjustment simultaneously.

Another modification may not execute inclination adjustment but execute only height adjustment to place the imaging element 17 in the focusing range while maintaining the reference attitude.

(l) The above embodiments employ a CCD image sensor as the imaging element 17 of the camera 15. The imaging element 17 is, however, not limited to this example of the embodiments but may be, for example, a CMOS image sensor.

The configuration of the above embodiments is provided with the first imaging area K1 and the second imaging area K2 by dividing the area of one imaging element 17. This configuration is, however, not restrictive. For example, one modified configuration may respectively allocate a plurality of imaging elements provided on one circuit board to the first imaging area K1 and the second imaging area K2. At least a single camera 15 (identical optical system) provides similar functions and advantageous effects to the functions and the advantageous effects of the above embodiments.

(m) According to the above embodiments, color image data (luminance image data) is used for the process of extracting various measurement object areas. The color image data may be used for another application, in place of or in addition to this application. For example, a modified configuration may map color image data to three-dimensional data obtained by three-dimensional measurement. This modified configuration enables the light and shade of a measured object to be expressed and thereby improves the texture of the three-dimensional image. As a result, this enables the shape of the measured object to be readily recognized instantly and significantly reduces the time required for the check operation.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

1 . . . printed circuit board, 4 . . . solder paste, 10 . . . substrate inspection apparatus, 13 . . . conveyor, 14 . . . illumination device, 14A-14I . . . lighting units, 15 . . . camera, 16 . . . control device, 17 . . . imaging element, 18 . . . both-sided telecentric optical system, 24 . . . image data storage device, 31 . . . object-side lens, 32 . . . aperture diaphragm, 33 . . . image-side lens, Ga . . . upper limit of focusing range, Gb . . . lower limit of focusing range, K1 . . . first imaging area, K2 . . . second imaging area, W . . . imaging range, W1 . . . first imaging range, W2 . . . second imaging range

The invention claimed is:

1. A three-dimensional measurement device, comprising:
an illuminator that irradiates a measured object with a predetermined light;
an imaging device comprising:
an imaging sensor displaceable at least in a vertical direction; and
a both-sided telecentric optical system that causes the imaging sensor to form an image of a predetermined area on the measured object irradiated with the predetermined light;
a conveyor that moves the illuminator and the imaging device relative to the measured object; and
a controller that:
executes three-dimensional measurement of a predetermined measurement object on the measured object, based on the image taken by the imaging device;
measures a height of the predetermined area at least at a time prior to imaging of the predetermined area on the measured object under the predetermined light; and
adjusts a height position of the imaging sensor based on a measurement result until an interval between the predetermined area and the imaging sensor becomes equal to a predetermined distance for imaging of the predetermined area, wherein
the controller measures an inclination of the predetermined area at least at the time prior to imaging of the predetermined area on the measured object under the predetermined light, and
the controller adjusts an inclination of the imaging sensor based on a measurement result until the inclination of the imaging sensor to correspond to the inclination of the predetermined area for imaging of the predetermined area.

2. The three-dimensional measurement device according to claim 1, wherein
the controller corrects the image taken by the imaging device, based on an amount of positional deviation in a horizontal direction of each pixel when the imaging sensor is inclined.

3. The three-dimensional measurement device according to claim 1, wherein
the conveyor reciprocates the illuminator and the imaging device relative to the measured object along a predetermined direction,
the controller measures, in a forward path, the predetermined area on the measured object, and
the controller adjusts the predetermined area and the imaging device takes the image under the predetermined light in a backward path.

4. The three-dimensional measurement device according to claim 2, wherein
the conveyor reciprocates the illuminator and the imaging device relative to the measured object along a predetermined direction,
the controller measures, in a forward path, the predetermined area on the measured object, and
the controller adjusts the predetermined area and the imaging device takes the image under the predetermined light in a backward path.

5. The three-dimensional measurement device according to claim 1, wherein the measured object is a printed circuit board on which solder paste is printed.

6. The three-dimensional measurement device according to claim 2, wherein the measured object is a printed circuit board on which solder paste is printed.

7. The three-dimensional measurement device according to claim 3, wherein the measured object is a printed circuit board on which solder paste is printed.

8. The three-dimensional measurement device according to claim 4, wherein the measured object is a printed circuit board on which solder paste is printed.

9. The three-dimensional measurement device according to claim 1, wherein the measured object is a wafer substrate on which solder bump is formed.

10. A three-dimensional measurement device, comprising:
an illuminator that irradiates a measured object with a predetermined light;
an imaging device comprising:
an imaging sensor displaceable at least in a vertical direction; and
a both-sided telecentric optical system that causes the imaging sensor to form an image of a predetermined area on the measured object irradiated with the predetermined light;
a conveyor that moves the illuminator and the imaging device relative to the measured object; and
a controller that:
executes three-dimensional measurement of a predetermined measurement object on the measured object, based on the image taken by the imaging device;
measures a height of the predetermined area at least at a time prior to imaging of the predetermined area on the measured object under the predetermined light; and
adjusts a height position of the imaging sensor based on a measurement result, without changing a height position of the both-sided telecentric optical system, until an interval between the predetermined area and the imaging sensor becomes equal to a predetermined distance for imaging of the predetermined area.

11. The three-dimensional measurement device according to claim 10, wherein
the controller measures an inclination of the predetermined area at least at the time prior to imaging of the predetermined area on the measured object under the predetermined light, and
the controller adjusts an inclination of the imaging sensor based on a measurement result until the inclination of the imaging sensor to correspond to the inclination of the predetermined area for imaging of the predetermined area.

12. The three-dimensional measurement device according to claim 11, wherein
the controller corrects the image taken by the imaging device, based on an amount of positional deviation in a horizontal direction of each pixel when the imaging sensor is inclined.

13. The three-dimensional measurement device according to claim 10, wherein
the conveyor reciprocates the illuminator and the imaging device relative to the measured object along a predetermined direction,
the controller measures, in a forward path, the predetermined area on the measured object, and
the controller adjusts the predetermined area and the imaging device takes the image under the predetermined light in a backward path.

14. The three-dimensional measurement device according to claim 11, wherein
the conveyor reciprocates the illuminator and the imaging device relative to the measured object along a predetermined direction,
the controller measures, in a forward path, the predetermined area on the measured object, and
the controller adjusts the predetermined area and the imaging device takes the image under the predetermined light in a backward path.

15. The three-dimensional measurement device according to claim 12, wherein
the conveyor reciprocates the illuminator and the imaging device relative to the measured object along a predetermined direction,
the controller measures, in a forward path, the predetermined area on the measured object, and
the controller adjusts the predetermined area and the imaging device takes the image under the predetermined light in a backward path.

16. The three-dimensional measurement device according to claim 10, wherein the measured object is a printed circuit board on which solder paste is printed.

17. The three-dimensional measurement device according to claim 10, wherein the measured object is a wafer substrate on which solder bump is formed.

* * * * *